(12) United States Patent
Du et al.

(10) Patent No.: US 9,610,045 B2
(45) Date of Patent: Apr. 4, 2017

(54) DETECTION OF VALID SIGNALS VERSUS ARTIFACTS IN A MULTICHANNEL MAPPING SYSTEM

(71) Applicant: Medtronic, Inc., Minneapolis, MN (US)

(72) Inventors: Juan Du, Minneapolis, MN (US); Subham Ghosh, Blaine, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 14/815,537

(22) Filed: Jul. 31, 2015

(65) Prior Publication Data
US 2017/0027524 A1    Feb. 2, 2017

(51) Int. Cl.
*A61B 5/04*    (2006.01)
*A61B 5/00*    (2006.01)
(Continued)

(52) U.S. Cl.
CPC ............ *A61B 5/7221* (2013.01); *A61B 5/044* (2013.01); *A61B 5/04012* (2013.01);
(Continued)

(58) Field of Classification Search
None
See application file for complete search history.

(56) References Cited

U.S. PATENT DOCUMENTS 5,117,824 A    6/1992    Keimel et al.
5,545,186 A    8/1996    Olson et al.
(Continued)

FOREIGN PATENT DOCUMENTS

CN    1859870 A    11/2006
CN    103052356 A    4/2013
(Continued)

OTHER PUBLICATIONS (PCT/US2016/032365) PCT Notification of Transmittal of the International Search Report and the Written Opinion of the International Searching Authority, Mailed Oct. 6, 2016, 10 pages.

*Primary Examiner* — Brian T Gedeon
*Assistant Examiner* — Ankit D Tejani
(74) *Attorney, Agent, or Firm* — Carol F. Barry

(57) ABSTRACT

A system and associated method is disclosed for determining whether signal is valid. The system comprises an electrode apparatus comprising a plurality of electrodes configured to be located proximate tissue of a patient. A display apparatus comprising a graphical user interface, wherein the graphical user interface is configured to present information to a user. A computing apparatus coupled to the electrode apparatus and display apparatus, wherein the computing apparatus is configured to determine whether a signal acquired from a channel associated with an electrode from the plurality of electrodes is valid and sufficiently strong by i) calculating a first derivative of the signal; ii) determining a minimum and maximum derivative from the first derivative; iii) determining whether signs of the minimum and maximum derivative are different; and in response to determining whether the signs of the minimum and maximum derivative are different, displaying on a display apparatus whether the signal is valid.

25 Claims, 27 Drawing Sheets

(51) Int. Cl.
*A61B 5/0408* (2006.01)
*A61B 5/044* (2006.01)
*A61N 1/37* (2006.01)

(52) U.S. Cl.
CPC ........ *A61B 5/04085* (2013.01); *A61B 5/6823* (2013.01); *A61B 5/7239* (2013.01); *A61N 1/3702* (2013.01)

(56) References Cited

U.S. PATENT DOCUMENTS

| | | |
|---|---|---|
| 5,738,104 A | 4/1998 | Lo et al. |
| 5,755,736 A | 5/1998 | Gillberg et al. |
| 6,263,235 B1 | 7/2001 | Kaiser et al. |
| 7,392,085 B2 | 6/2008 | Warren et al. |
| 7,587,074 B2 | 9/2009 | Zarkh et al. |
| 7,627,367 B2 | 12/2009 | Warren et al. |
| 7,941,213 B2 | 5/2011 | Markowitz et al. |
| 7,953,489 B2 | 5/2011 | Warren et al. |
| 8,106,905 B2 | 1/2012 | Markowitz et al. |
| 8,135,467 B2 | 3/2012 | Markowitz et al. |
| 8,185,192 B2 | 5/2012 | Markowitz et al. |
| 8,208,991 B2 | 6/2012 | Markowitz et al. |
| 8,214,018 B2 | 7/2012 | Markowitz et al. |
| 8,260,395 B2 | 9/2012 | Markowitz et al. |
| 8,340,751 B2 | 12/2012 | Markowitz et al. |
| 8,345,067 B2 | 1/2013 | Markowitz et al. |
| 8,355,774 B2 | 1/2013 | Markowitz et al. |
| 8,364,252 B2 | 1/2013 | Markowitz et al. |
| 8,391,965 B2 | 3/2013 | Markowitz et al. |
| 8,421,799 B2 | 4/2013 | Markowitz et al. |
| 8,424,536 B2 | 4/2013 | Markowitz et al. |
| 8,442,625 B2 | 5/2013 | Markowitz et al. |
| 8,457,371 B2 | 6/2013 | Markowitz et al. |
| 8,494,608 B2 | 7/2013 | Markowitz et al. |
| 8,494,613 B2 | 7/2013 | Markowitz et al. |
| 8,494,614 B2 | 7/2013 | Markowitz et al. |
| 8,532,734 B2 | 9/2013 | Markowitz et al. |
| 8,560,042 B2 | 10/2013 | Markowitz et al. |
| 8,660,640 B2 | 2/2014 | Markowitz et al. |
| 8,663,120 B2 | 3/2014 | Markowitz et al. |
| 8,768,434 B2 | 7/2014 | Markowitz et al. |
| 8,825,157 B2 | 9/2014 | Warren et al. |
| 8,831,701 B2 | 9/2014 | Markowitz et al. |
| 8,839,798 B2 | 9/2014 | Markowitz et al. |
| 8,843,189 B2 | 9/2014 | Markowitz et al. |
| 8,887,736 B2 | 11/2014 | Markowitz et al. |
| 8,923,963 B2 | 12/2014 | Bonner et al. |
| 9,107,584 B2 | 8/2015 | Wohlschlager et al. |
| 9,254,389 B2 | 2/2016 | Hincapie Ordonez et al. |
| 9,265,954 B2 | 2/2016 | Ghosh |
| 9,307,928 B1 | 4/2016 | Al-Ali et al. |
| 2005/0038478 A1* | 2/2005 | Klepfer ................ A61N 1/3622 607/9 |
| 2005/0049644 A1 | 3/2005 | Warren et al. |
| 2005/0192507 A1 | 9/2005 | Warren et al. |
| 2008/0275521 A1 | 11/2008 | Warren et al. |
| 2009/0093857 A1 | 4/2009 | Markowitz et al. |
| 2009/0216144 A1 | 8/2009 | Hopenfeld |
| 2009/0262109 A1 | 10/2009 | Markowitz et al. |
| 2009/0262979 A1 | 10/2009 | Markowitz et al. |
| 2009/0262980 A1 | 10/2009 | Markowitz et al. |
| 2009/0262992 A1 | 10/2009 | Markowitz et al. |
| 2009/0264128 A1 | 10/2009 | Markowitz et al. |
| 2009/0264727 A1 | 10/2009 | Markowitz et al. |
| 2009/0264738 A1 | 10/2009 | Markowitz et al. |
| 2009/0264739 A1 | 10/2009 | Markowitz et al. |
| 2009/0264741 A1 | 10/2009 | Markowitz et al. |
| 2009/0264742 A1 | 10/2009 | Markowitz et al. |
| 2009/0264743 A1 | 10/2009 | Markowitz et al. |
| 2009/0264746 A1 | 10/2009 | Markowitz et al. |
| 2009/0264747 A1 | 10/2009 | Markowitz et al. |
| 2009/0264748 A1 | 10/2009 | Markowitz et al. |
| 2009/0264749 A1 | 10/2009 | Markowitz et al. |
| 2009/0264750 A1 | 10/2009 | Markowitz et al. |
| 2009/0264751 A1 | 10/2009 | Markowitz et al. |
| 2009/0264752 A1 | 10/2009 | Markowitz et al. |
| 2009/0264777 A1 | 10/2009 | Markowitz et al. |
| 2009/0264778 A1 | 10/2009 | Markowitz et al. |
| 2009/0297001 A1 | 12/2009 | Markowitz et al. |
| 2009/0299429 A1* | 12/2009 | Mayotte ............ A61N 1/36564 607/18 |
| 2010/0004724 A1 | 1/2010 | Markowitz et al. |
| 2010/0076513 A1 | 3/2010 | Warren et al. |
| 2011/0054293 A1 | 3/2011 | Markowitz et al. |
| 2011/0054304 A1 | 3/2011 | Markowitz et al. |
| 2011/0106203 A1 | 5/2011 | Markowitz et al. |
| 2011/0172729 A1 | 7/2011 | Sweeney et al. |
| 2012/0130232 A1 | 5/2012 | Markowitz et al. |
| 2012/0190993 A1 | 7/2012 | Markowitz et al. |
| 2012/0283587 A1 | 11/2012 | Ghosh et al. |
| 2014/0088661 A1 | 3/2014 | Hincapie Ordonez et al. |
| 2014/0277247 A1 | 9/2014 | Stadler et al. |
| 2014/0323882 A1 | 10/2014 | Ghosh et al. |
| 2014/0323892 A1 | 10/2014 | Ghosh et al. |
| 2014/0323893 A1* | 10/2014 | Ghosh .................... A61B 5/044 600/510 |
| 2014/0350618 A1 | 11/2014 | Warren et al. |
| 2015/0032172 A1 | 1/2015 | Ghosh |
| 2015/0157225 A1 | 6/2015 | Gillberg et al. |
| 2015/0157231 A1 | 6/2015 | Gillberg et al. |
| 2015/0202443 A1* | 7/2015 | Zielinski ............. A61N 1/3682 607/18 |
| 2016/0030743 A1 | 2/2016 | Kaiser |
| 2016/0051186 A1 | 2/2016 | Kaib et al. |
| 2016/0067489 A1 | 3/2016 | Ramanathan et al. |
| 2016/0067498 A1 | 3/2016 | Ghosh |
| 2016/0081573 A1 | 3/2016 | Niebauer et al. |
| 2016/0120431 A1 | 5/2016 | Habte et al. |

FOREIGN PATENT DOCUMENTS

| | | |
|---|---|---|
| EP | 1774906 A1 | 4/2007 |
| EP | 1659934 B1 | 11/2008 |
| EP | 1774906 B1 | 5/2013 |
| JP | 2013252423 A | 12/2013 |
| WO | 03014631 A1 | 5/2003 |
| WO | 2005011809 A2 | 2/2005 |
| WO | 2010014063 A1 | 2/2010 |
| WO | 2012017364 A1 | 2/2012 |
| WO | 2012106067 A1 | 8/2012 |

\* cited by examiner

DETECTION OF VALID SIGNALS VERSUS ARTIFACTS IN A MULTICHANNEL MAPPING SYSTEM

RELATED APPLICATION

Cross-reference is hereby made to commonly assigned U.S. patent application Ser. No. 14/815,506, filed on even date herewith entitled "DETERMINING ONSET OF CARDIAC DEPOLARIZATION AND REPOLARIZATION WAVES FOR SIGNAL PROCESSING", U.S. patent application Ser. No. 14/815,478, filed on even date herewith entitled "IDENTIFYING AMBIGUOUS CARDIAC SIGNALS FOR ELECTROPHYSIOLOGIC MAPPING", and incorporated by reference in their entirety.

TECHNICAL FIELD

The present disclosure relates to medical devices, and more particularly, to medical devices for sensing, detection, and analysis of cardiac signals.

BACKGROUND

Implantable medical devices (IMDs), such as implantable pacemakers, cardioverters, defibrillators, or pacemaker-cardioverter-defibrillators, provide therapeutic electrical stimulation to the heart. IMDs may provide pacing to address bradycardia, or pacing or shocks in order to terminate tachyarrhythmia, such as tachycardia or fibrillation. In some cases, the medical device may sense intrinsic depolarizations of the heart, detect arrhythmia based on the intrinsic depolarizations (or absence thereof), and control delivery of electrical stimulation to the heart if arrhythmia is detected based on the intrinsic depolarizations.

IMDs may also provide cardiac resynchronization therapy (CRT), which is a form of pacing. CRT involves the delivery of pacing to the left ventricle, or both the left and right ventricles. The timing and location of the delivery of pacing pulses to the ventricle(s) may be selected to improve the coordination and efficiency of ventricular contraction.

IMDs sense signals and deliver therapeutic stimulation via electrodes. Implantable pacemakers, cardioverters, defibrillators, or pacemaker-cardioverter-defibrillators are typically coupled to one or more subcutaneous electrodes or intracardiac leads that carry electrodes for cardiac sensing and delivery of therapeutic stimulation. The signals sensed via the electrodes may be referred to as a cardiac electrogram (EGM) and may include the depolarizations, repolarizations, and other intrinsic electrical activity of the heart.

Systems for implanting medical devices may include workstations or other equipment in addition to the medical device itself. In some cases, these other pieces of equipment assist the physician or other technician with placing the intracardiac leads at particular locations on the heart. In some cases, the equipment provides information to the physician about the electrical activity of the heart and the location of the intracardiac lead. The equipment may perform similar functions as the medical device, including delivering electrical stimulation to the heart and sensing the depolarizations of the heart. In some cases, the equipment may include equipment for obtaining an electrocardiogram (ECG) via skin electrodes placed on the surface of the patient. In addition, the patient may have a plurality of electrodes on an ECG belt or vest that surrounds the torso of the patient. After the vest has been secured to the torso, a physician can perform a series of tests to evaluate a patient's cardiac response.

During the evaluation process, a physician typically needs to review the onset of cardiac depolarization waves in the rhythms using a computing apparatus. Numerous methods are used to detect onset of depolarization waves. U.S. Pat. No. 8,781,580B2 to Sven-Erik Hedberg et al. is directed to pacing sequence optimization applied through the multipolar LV lead based on a particular optimization criterion which is the time point of the onset of activation of the left ventricle until closure of the mitral valve of the heart. The pacing sequence that minimizes the time interval from onset of LV activation until the mitral valve closure is identified and used as currently optimal pacing sequence for the IMD. An activation detector is configured to detect onset of activation of the left ventricle for a cardiac cycle. The activation detector is configured to detect onset of contraction of the left ventricle for the cardiac cycle based on i) a signal received by the connector for a connectable sensor or ii) an impedance signal determined by the activity detector based on an electric signal received by the connector from a connectable pacing electrode. Nowhere in this method does it eliminate polarization artifacts to ensure the best channel is selected or adjust detection of the onset of cardiac depolarization to ensure beats are not missed.

Additionally, the Sven-Erik Hedberg method does not address ambiguous cardiac signals. U.S. Pat. No. 7,953,489 B2 to Warren et al. Warren et al does correct for ambiguous signals, defined as sensed cardiac electrical signal that are difficult to comprehend, understand, or classify by an implantable medical device (IMD) (e.g. ICD etc.) system's detection architecture. Warren et al, addresses ambiguous signals by counting to characteristic features, comparing the ambiguous signal to a threshold, and then sensing alternate cardiac signals. This method can be cumbersome since the characteristic features need to be parsed and counted.

It is therefore desirable to develop additional methods and systems for signal processing that allows the system to acquire cardiac signals with little or no artifacts and/or ambiguous signals thereby allowing physicians to more accurately determine therapy for a patient.

SUMMARY

The present disclosure assists in eliminating invalid signals associated with cardiac signals acquired from one or more electrodes associated with an electrode apparatus. By eliminating invalid signals (e.g. artifacts etc.), techniques and methods described herein substantially increase the accuracy of the onset of each heart depolarization over conventional threshold detection methods.

A system and associated method is disclosed for determining whether signal is valid. The system comprises an electrode apparatus comprising a plurality of electrodes configured to be located proximate tissue of a patient. A display apparatus comprising a graphical user interface, wherein the graphical user interface is configured to present information to a user. A computing apparatus coupled to the electrode apparatus and display apparatus, wherein the computing apparatus is configured to determine whether a signal acquired from a channel associated with an electrode from the plurality of electrodes is valid and sufficiently strong by i) calculating a first derivative of the signal; ii) determining a minimum and maximum derivative from the first derivative; iii) determining whether signs of the minimum and maximum derivative are different; and in response to determining whether the signs of the minimum and maximum derivative are different, displaying on a display apparatus whether the signal is valid.

DETAILED DESCRIPTION

Exemplary systems, methods, and interfaces shall be described with reference to FIGS. 1-35. It will be apparent to one skilled in the art that elements or processes from one embodiment may be used in combination with elements or processes of the other embodiments, and that the possible embodiments of such methods, apparatus, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Figure 3:
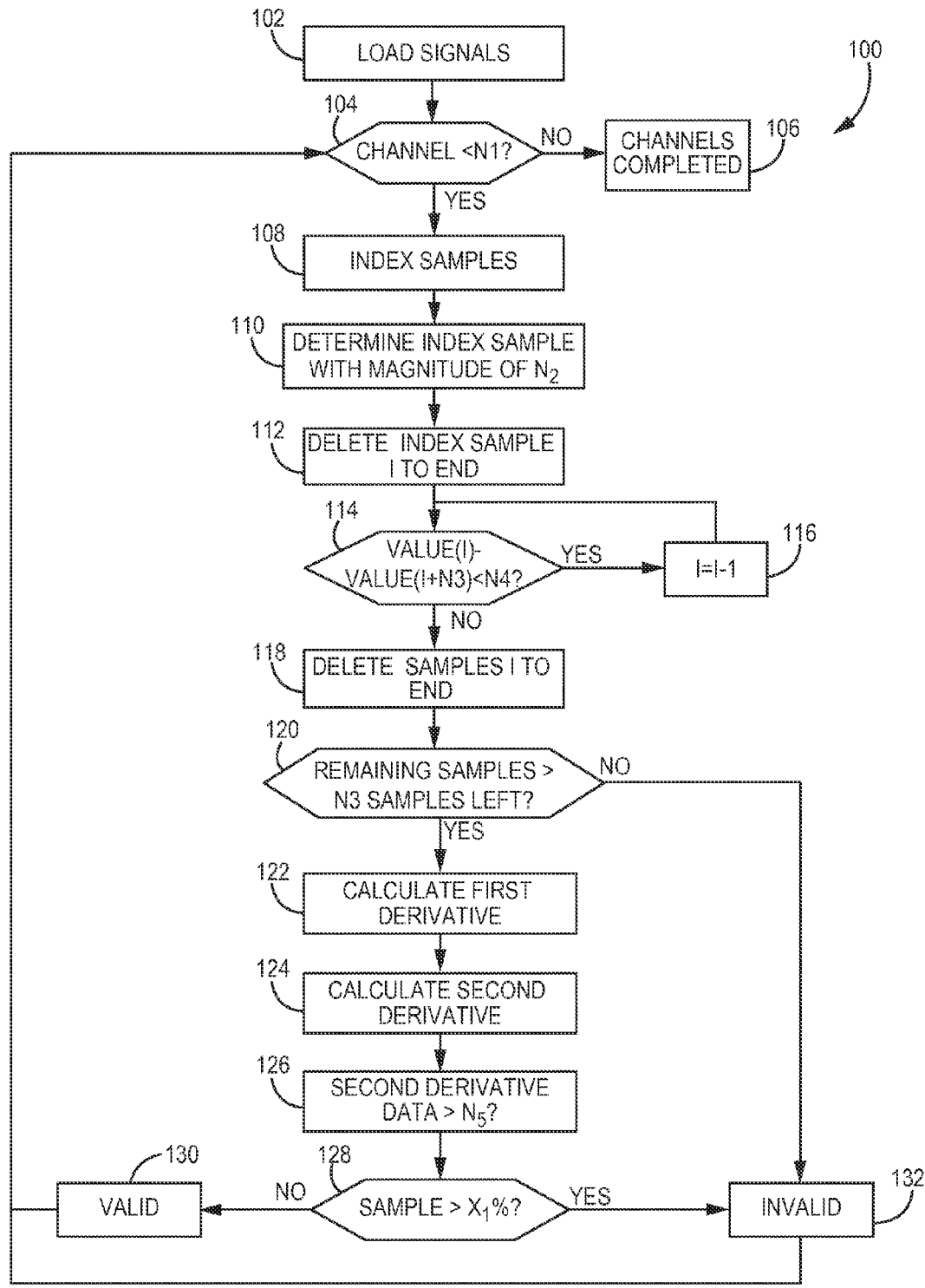
FIG. 3 is a flow diagram for validating electrocardiograms (ECG) data acquired from a plurality of channels and eliminating data that is deemed invalid.
Figure 4:
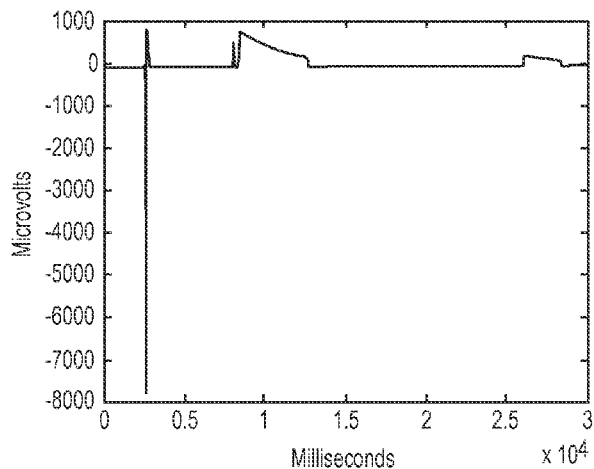
FIG. 4 is a graph illustrating an example cardiac ECG that shows invalid data that is excluded by the method depicted in FIG. 3.
Figure 7:
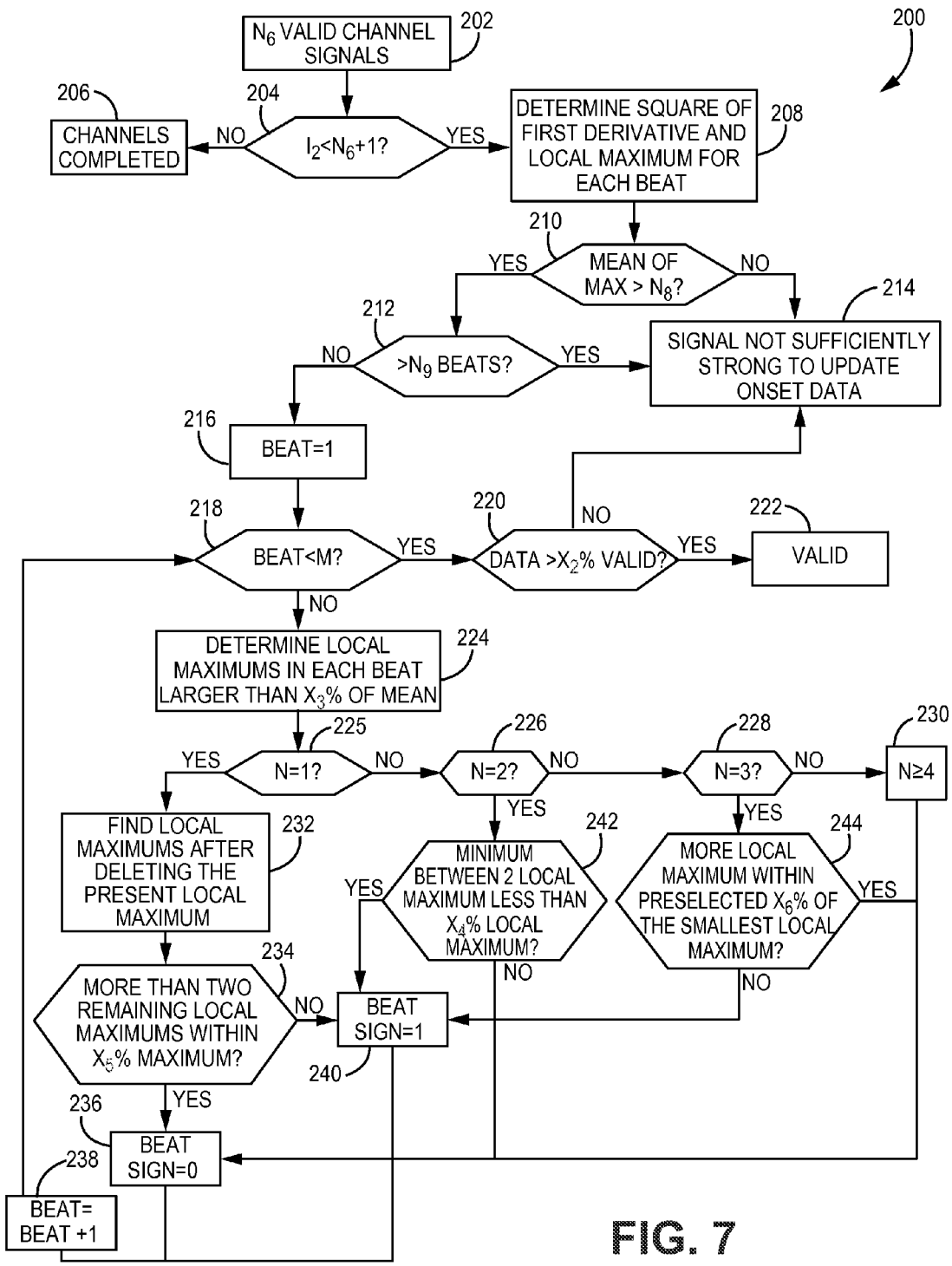
FIG. 7 is a flow diagram for detecting a signal that exhibits a strong fidelity of a signal.
Figure 10:
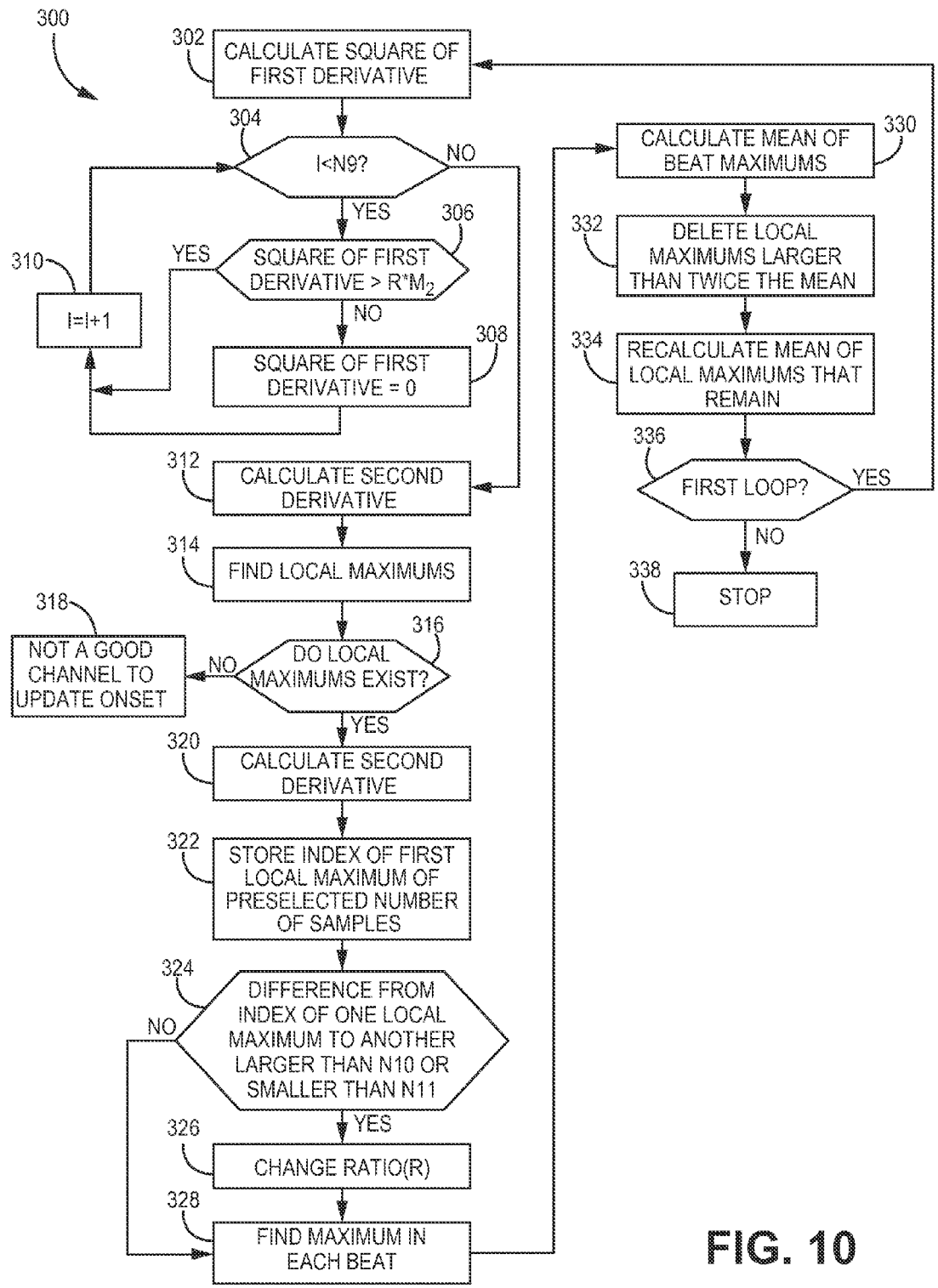
FIG. 10 is a flow diagram illustrating an example technique for determining beat information such as a maximum for each beat acquired from a signal on a channel.

One or more embodiments of the present disclosure is embodied in methods 100-300, depicted in FIGS. 3, 7, and 10, which ensures that the most accurate data acquired from an electrode apparatus is used to update onset data for each beat. Accuracy of the onset data is improved by eliminating noise (e.g. artifacts) that can obscure signals.

Figure 25:
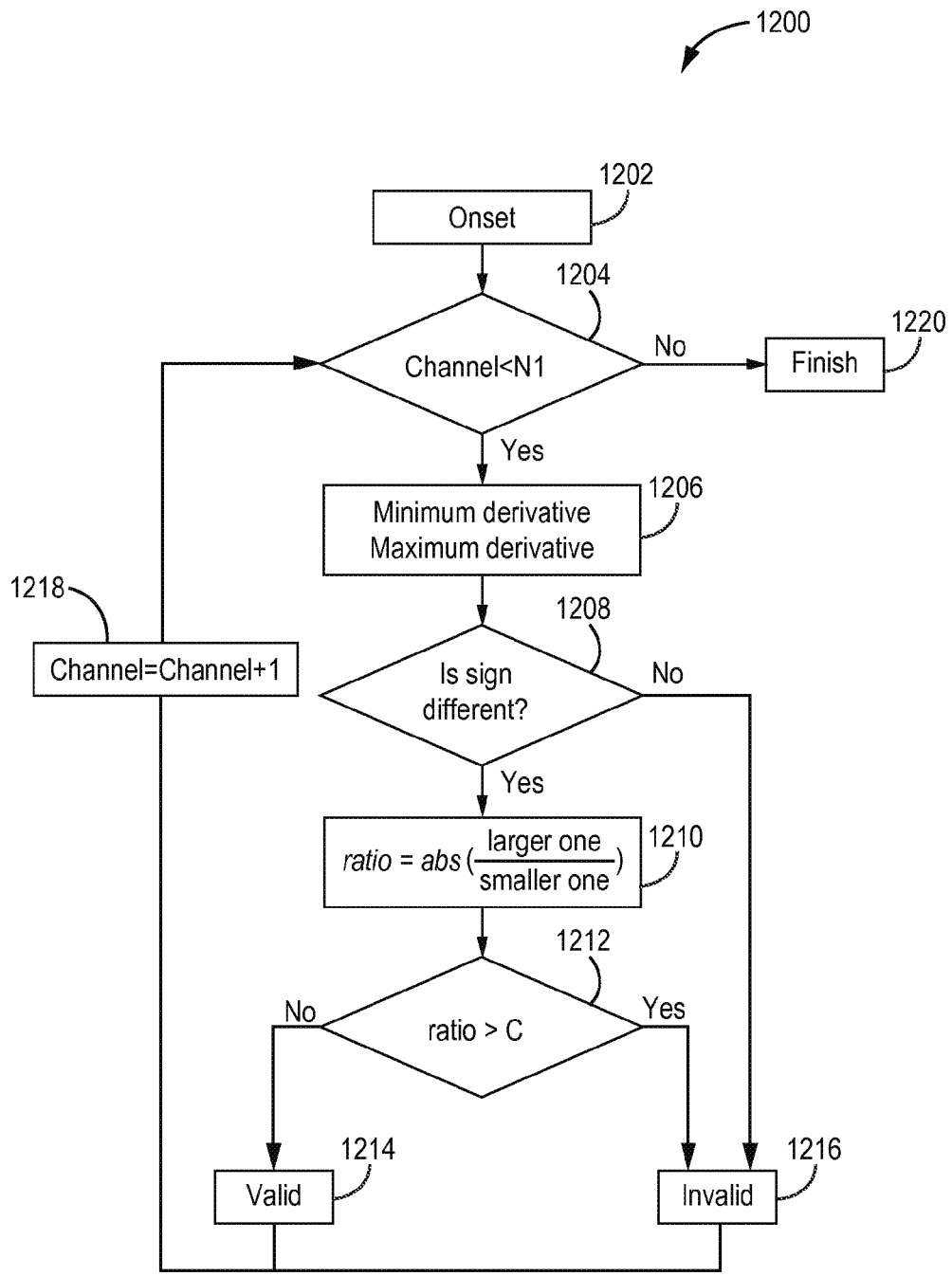
FIG. 25 is a flow diagram for validating electrocardiograms (ECG) data acquired from a plurality of channels and eliminating data that is deemed invalid due to artifacts.
Figure 29:
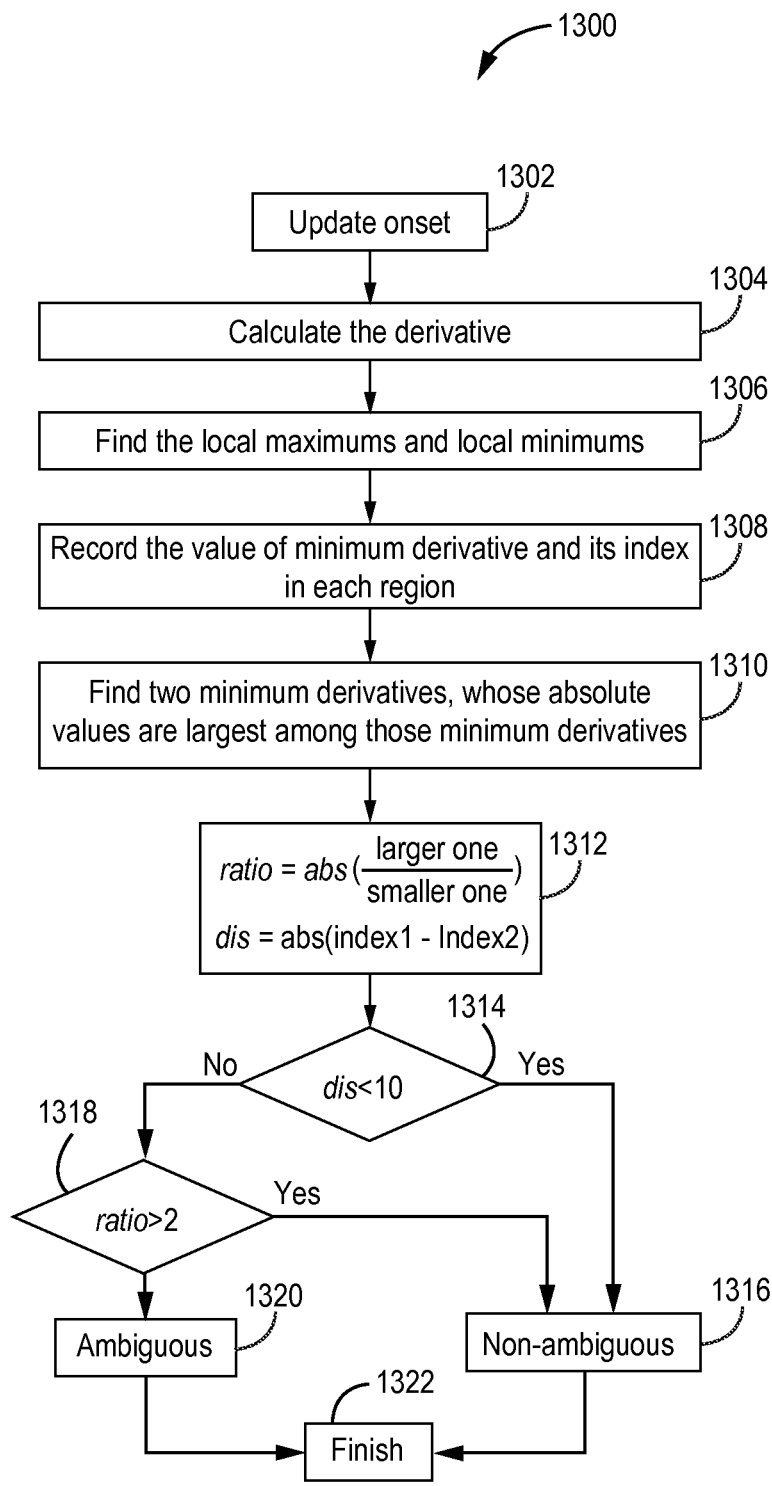
FIG. 29 depicts a method for identifying ambiguous cardiac signals during electrophysiologic mapping.

One or more other embodiments depicted in FIGS. 25 and 29 are implemented after the onset data has been updated. FIG. 25, for example, validates electrocardiograms (ECG) data acquired from a plurality of channels and eliminates data that is deemed invalid due to artifacts. FIG. 29 serves to identify ambiguous cardiac signals and locates channels that provide non-ambiguous signals. The teachings of FIG. 29 can also be applied to the signal processing techniques described relative to FIGS. 3, 7, and 10 and/or FIG. 25.

Alternatively, FIG. 29 can independently be applied to a cardiac signal without the processing techniques FIGS. 3, 7, and 10 and/or FIG. 25 being used before or after FIG. 29. The remaining diagrams depict the hardware and/or details as to implementation of the methods described herein.

Figure 1:
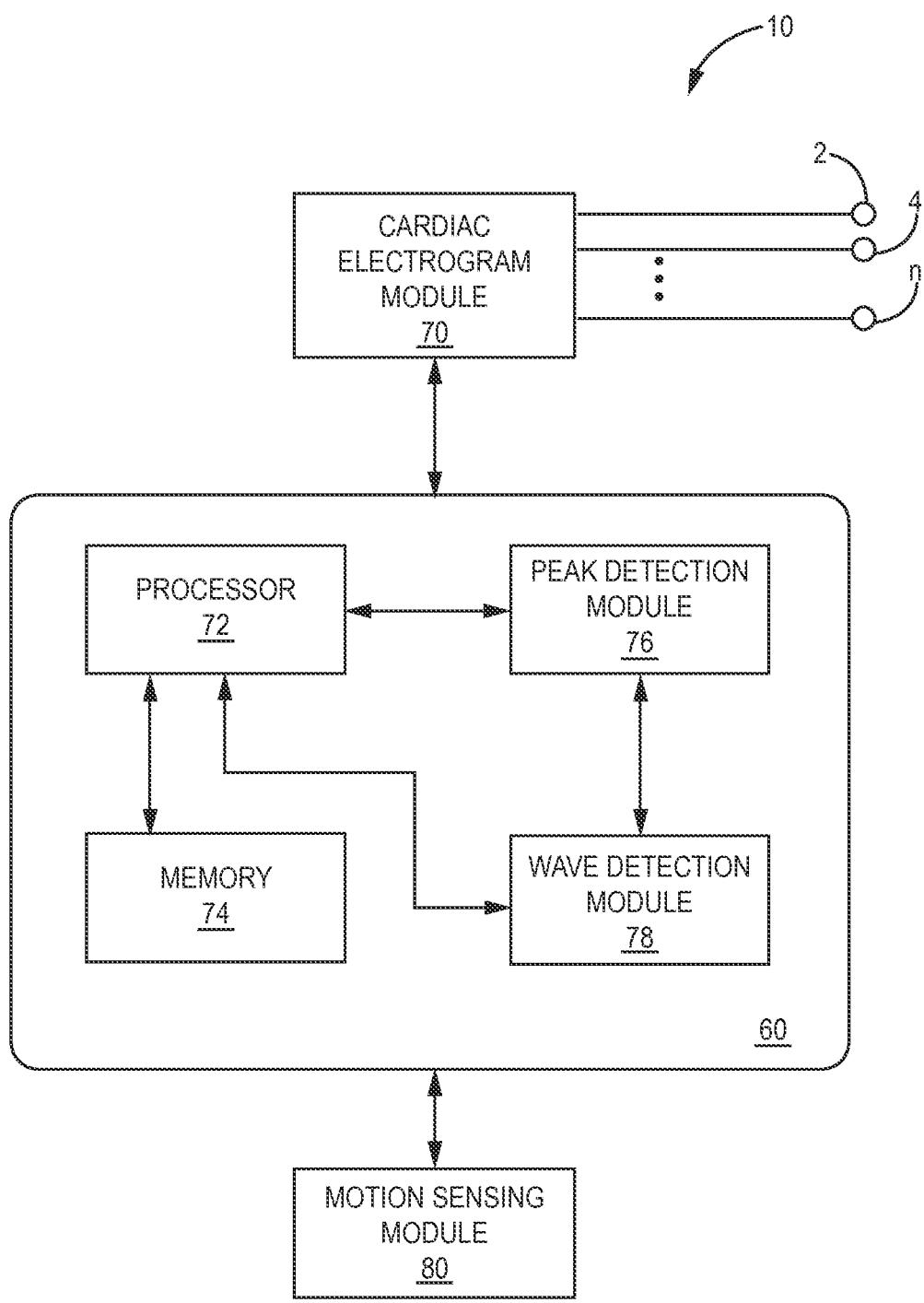
FIG. 1 is a block diagram illustrating and example system that may determine the onsets and offsets of various heart repolarization and depolarization waves.

FIG. 1 is a block diagram illustrating an example configuration of a system for determining the onsets and/or offsets of heart depolarization and repolarizations waves. In the illustrated example, system 10 includes a device 60, a cardiac electrogram module 70, and a motion sensing module 80. Device 60 may further include a processor 72, a memory 74, a peak detection module 76, and a wave detection module 78.

Processor 72 may include any one or more of a microprocessor, a controller, a digital signal processor (DSP), an application specific integrated circuit (ASIC), a field-programmable gate array (FPGA), or equivalent discrete or analog logic circuitry. In some examples, processor 72 may include multiple components, such as any combination of one or more microprocessors, one or more controllers, one or more DSPs, one or more ASICs, or one or more FPGAs, as well as other discrete or integrated logic circuitry. The functions attributed to processor 72 herein may be embodied as software, firmware, hardware or any combination thereof. Generally, processor 72 controls cardiac electrogram module 70, peak detection module 76, wave detection module 78, and motion sensing module 80 to determine timings of the onsets and offsets of heart depolarization and/or repolarizations waves. Processor 72 can perform calculations, determinations, comparisons of data etc.

In general, a heart produces a repetitive electrical signal which causes the heart to mechanically contract, thereby pumping blood throughout the body. Generally, the signal may be detected and displayed as a cardiac electrogram signal. Although the exact representation may differ depending on the placement of leads on or within the body to detect the heart signal, among other factors, a common cardiac electrogram includes several recognizable features. The initial deflections of the signal represent the P-wave and the QRS complex. The P-wave represents the depolarization of the atria and the QRS complex represents the depolarization of the ventricles. The Q-wave of the QRS complex is the initial downward deflection of the signal during the complex. Following the Q-wave is the R-wave, which is an upward deflection of the signal. Finally, the S-wave is another downward deflection. The next portion of the signal represents repolarization of the atria and ventricles. More specifically, what is generally called the T-wave represents the repolarization of the ventricles. There is no specific wave or feature of the signal that represents the repolarization of the atria because the generated signal is small in comparison to the T-wave. Together, the P-wave, the Q, R, and S waves, and the T-wave represent the depolarization and repolarization waves of a heart electrical signal.

Memory 74 includes computer-readable instructions that, when executed by processor 72, causes system 10 and processor 72 to perform various functions attributed to system 10 and processor 72 herein. Memory 74 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Generally, cardiac electrogram module 70 is configured sense or acquire electrical signals from a patient. Cardiac electrogram module 70 is electrically coupled to one or more electrodes 2, 4, 6, 8, 10, 12, 14 . . . n by one or more leads.

In some examples, the one or more electrodes 2, 4, 6, 8, 10, 12, 14 . . . n may be external electrodes, e.g., attached to the surface of a patient, or implanted at various locations within a patient, e.g., on or within a heart.

Figure 2:
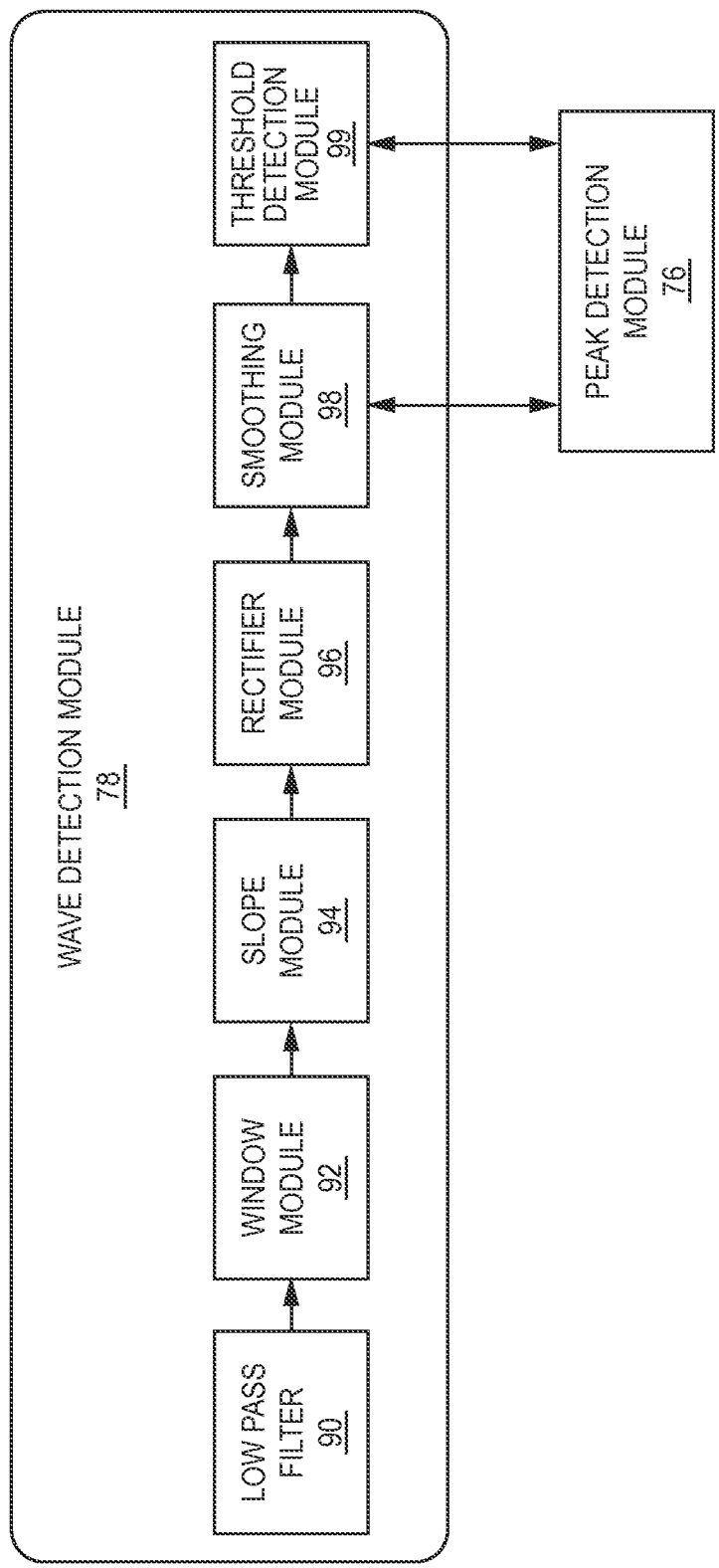
FIG. 2 is a block diagram illustrating an example configuration of a wave detection module.

Peak detection module 76 may be configured to determine a maximum value of a particular signal. For example, peak detection module 76 may be configured to receive the electrical signal from cardiac electrogram module 70 and determine the maximum value. In another example, as illustrated in FIG. 2, peak detection module 76 may be configured to receive a signal from wave detection module 78 and determine a maximum value.

Wave detection module 78 determines the onsets and/or offsets on the heart depolarization and repolarizations waves. Wave detection module 78 may be configured to receive an electrical signal. For example, wave detection module 78 may be configured to receive an electrical signal sensed by cardiac electrogram module 70. Motion sensing module 80 may detect mechanical motion of a heart, e.g., during contraction of the heart. Motion sensing module 80 may comprise one or more sensors that generate a signal that varies based on cardiac contraction or motion generally, such as one or more accelerometers, pressure sensors, impedance sensors, or flow sensors. Motion sensing module 80 may provide an indication of the timing of motion, e.g., contraction, to device 60, e.g., to processor 72. The detected contraction may be contraction of cardiac tissue at a particular location, e.g., a particular portion of a ventricular wall.

In some examples, motion sensing module 80 may be configured to image the heart, or electrodes, catheters, wires, or other radio-opaque markers in or on the heart and identify motion associated with contraction based on images of the heart. In some examples, motion sensing module 80 may be configured to direct ultrasound energy toward a patient's heart. Motion sensing module 80 may also be configured to detect any ultrasonic energy deflected back toward motion sensing module 80 by the patient's heart. In this manner, motion sensing module 80 may capture information about the mechanical motion (i.e. the contracting and relaxing of the ventricles and/or atria) of the heart. Systems and methods for identifying heart mechanical contractions are described in U.S. Pat. No. 7,587,074 to Zarkh et al., which issued on Sep. 8, 2009 and is entitled, "METHOD AND SYSTEM FOR IDENTIFYING OPTIMAL IMAGE WITHIN A SERIES OF IMAGES THAT DEPICT A MOVING ORGAN," and is incorporated herein by reference in its entirety.

Processor 72 may determine values of one or more metrics, such as cardiac intervals or cardiac electromechanical delay, based on the timing of onset and/or offset of a wave, as determined by wave detection module 78, and/or the timing of contraction, as determined by motion sensing module 80. For example, processor 72 may determine QRS width based on an onset and offset of the QRS complex as identified by wave detection module 78. As another example, processor 72 may determine a QT interval based on a QRS onset and T-wave onset identified by wave detection module 78. The processor may also determine the interval between the onset of depolarization on a surface ECG lead and the time of local electrical activation as sensed by a lead or a mapping catheter or guidewire at a site within the heart. Furthermore, as described in greater detail below, processor 72 may determine electromechanical delay based on a QRS onset identified by wave detection module 78 and an indication of the timing of cardiac contraction received from motion sensing module 80.

Figure 13:
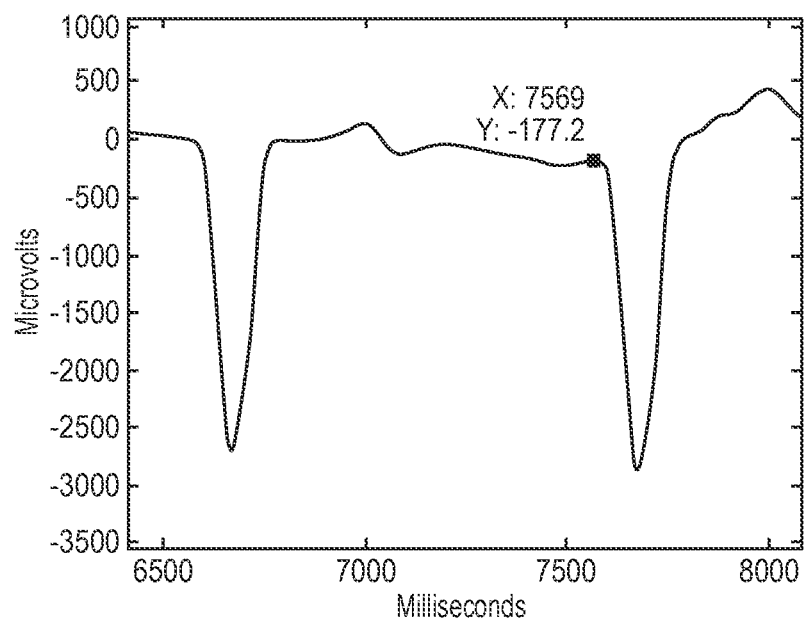
FIG. 13 is a graph diagram an example two different local maximums in which the onset of heart depolarization has been determined after performing methods 100-300 depicted in FIGS. 3, 7 and 10.

Although in FIG. 1 device 60, module 70, and module 80 are depicted as separate, in other examples the modules and device may be combined into fewer separate components. For example, as illustrated in FIG. 13, all of the functionality of system 10 may be combined into a single device.

Furthermore, although processor 72, peak detection module 76 and wave detection module 78 are depicted as separate functional modules in the example of FIG. 1, their collective functionality may be provided by any number of physical or logical processing elements provided by one or more co-located or networked devices. In one example, peak detection module 76 and wave detection module 78 may be functional modules executed by processor 72. Similarly in FIG. 2, although the various modules 90, 92, 94, 96, 98, and 99 are depicted as separate modules in a single device, in other examples their functionality may be provided by any one or more devices.

FIG. 2 is a block diagram illustrating an example configuration of wave detection module 78. In the example of FIG. 2, wave detection module 78 comprises a low-pass filter 90, a window module 92, a slope module 94, a rectifier module 96, a smoothing module 98, and a threshold detection module 99.

Low pass filter 90 may generally be any low-pass filter designed to reduce or eliminate the high frequency components of electrical signals. Some examples of low-pass filters embodied in hardware include capacitive low-pass filters and inductive low-pass filters. Other low-pass filters may be embodied entirely within software. In some embodiments, low-pass filter 90 is embodied as a combination of hardware and software. Low-pass filter 90 may be a first, second, or higher order filter. In some examples, low-pass filter 90 comprises multiple filters placed in a succession in order to create a desired frequency response. In some examples, the low-pass filter 90 is a linear filter with a maximally flat group delay or maximally linear phase response. A constant group delay is a characteristic of phase response of an analog or a digital filter, which helps preserve the shape of the signal in the pass-band. In at least one example, the low-pass filter is a Bessel filter with a cut-off frequency of 15 Hz.

Window module 92 may generally window received signals. In some examples, window module 92 may receive cardiac electrograms, and in further examples, some of the cardiac electrograms may include a marker or markers indicating one or more points of interest. Some example of points of interest could be the R-wave, the P-wave, or any other wave of the cardiac electrogram. In some examples, peak detection module 76 may detect the locations of R-waves in a cardiac electrogram, according to techniques that are well known in the art, for example using a varying threshold. Peak detection module 76 may then place a marker within the cardiac electrogram identifying the location of the R-wave. In other examples, other modules or devices may detect and mark waves in the cardiac electrogram. In examples where the signal includes at least one marker, window module 92 may window the received electrical signal around the marker. For example, window module 92 may multiply the received electrical signal by zero outside of the area around the marker and by one inside of the area around the marker. In this way, window module 92 may modify the received electrical signal to only contain information in an area around the marker. In some examples, window module 92 may isolate the QRS complex. In some examples, window module 92 may window an area of interest of equal length around the marker, for instance 150 ms before the marker and 150 ms after the marker. In other examples, the area in front of the marker may be longer or shorter than the area behind the marker. In one or more embodiments, the algorithm detects the local maximums as information for each beat. Specifically, each beat includes several local maximums which can represent, for example, the P wave, the QRS wave, and the T wave. Based on the beat information, the channels to update the onset of cardiac depolarization are selected. After updating the onset of cardiac depolarization, a window, extending a certain amount of time (e.g. 220 ms) is used to detect the activation time. The window can be adjusted by using the onset of cardiac depolarization. Since the window is dependent on the onset of cardiac depolarization, the window also changes with any changes to the onset of cardiac depolarization.

Slope module 94 may generally determine the slope of a received electrical signal. Some example techniques for determining a slope that slope module 94 may use are taking the simple difference between adjacent points on the received electrical signal, or determining the first derivative of the received electrical signal.

Rectifier module 96 may generally rectify a received electrical signal. For example, rectifier module 96 may half-wave rectify the received electrical signal to produce a resulting signal with information only where the original signal was above zero. In another example, rectifier module 96 may full-wave rectify the received electrical signal to produce a resulting signal where all the negative values of the original signal are now positive.

Smoothing module 98 may generally smooth a received electrical signal. For example, smoothing module 98 may be configured to increase the values of certain points and decrease the values of certain points so as to create a smoother signal. Some example smoothing algorithms include rectangular or un-weighted sliding average smoothing, triangular smoothing, and Savitzky-Golay smoothing. The smoothing algorithms may be implemented through one or more filters. In at least one example, the smoothing filter is 10-order median filter. In another example, the smoothing filter is a n-order median filter where n is an increasing linear function of the sampling frequency used to digitize the electrogram or electrocardiogram signals.

Threshold detection module 99 may generally be configured to determine a threshold and at what points a received electrical signal crosses a pre-determined threshold. The threshold may be determined based on a maximum value of the signal received from smoothing module 98. For example, as illustrated in FIG. 2, threshold detection module 99 may be configured to receive, from peak detection module 76, a maximum value of the signal received from smoothing module 98. Threshold detection module 99 may be configured to determine a threshold value based on the received maximum value. For example, threshold detection module 99 may determine the threshold to be ten percent, fifteen percent, twenty percent, or more of the maximum value. Ultimately, threshold detection module 98 may determine the onsets and/or offsets of heart depolarization and repolarizations waves based on at which points of a received electrical signal cross a threshold.

Methods 100-300, depicted in FIGS. 3, 7, and 10, ensure that the most accurate data is used to update onset data for each beat. Methods 100-300 determine onset of depolarization are based on acquiring unipolar cardiac signal from each electrode in response to delivering a pace to cardiac tissue. However, determination of onset of depolarization can also be determined solely on intrinsic rhythm (i.e. without sending a pacing pulse to test the reaction of the cardiac tissue). Onset of data for each beat is determined after implementing methods 100-300. For example, the first local maximum is located for each beat and then stored in memory as described relative to FIG. 35. The first derivative data that is smaller than a preselected percentage (e.g. 5% or less, 4% or less, 3% or less, 2% or less, 1% or less etc.) of this first local maximum is considered to be the onset of depolarization.

Method 100 is directed to validating ECG data acquired from a plurality of channels and eliminating channels that are deemed to acquire invalid data such as channels in which the electrode is detached from the surface of skin of a patient. Electrodes detached from the skin produces noise.

The total number of channels used in method 100 is automatically preset or set by the user and stored into memory. For the sake of illustration, in one example, the total number of channels, from which time sampled signal data is acquired, is set to N1 (e.g. 55). In one or more embodiments, a preferred range of 30 to 50 channels are employed. It should be understood however, that the total number of channels could be any integer in the range of 1-500 channels. In one or more embodiments, the total number of channels can be less than or equal to the following number of total channels: 500 channels, 450 channels, 400 channels, 350 channels, 300 channels, 250 channels, 200 channels, 150 channels, 100 channels, 90 channels, 80 channels, 70 channels, 60 channels, 50 channels, 40 channels, 30 channels, 20 channels, etc. Additionally, method 100 requires counters to be automatically initialized by setting each counter to preselected values (e.g. I counter is set to 0, etc.).

Referring to block 102 of FIG. 3, signals are acquired and loaded into memory from electrodes such as body surface electrodes and/or electrodes that are implanted in a patient's body through an IMD, leadless pacemaker, and/or medical electrical lead. An exemplary leadless pacemaker is shown and described in U.S. Pat. No. 8,923,963B2, issued Dec. 30, 2014 and assigned to the assignee of the present invention, the disclosure of which is incorporated by reference in its entirety herein.

Figure 20:
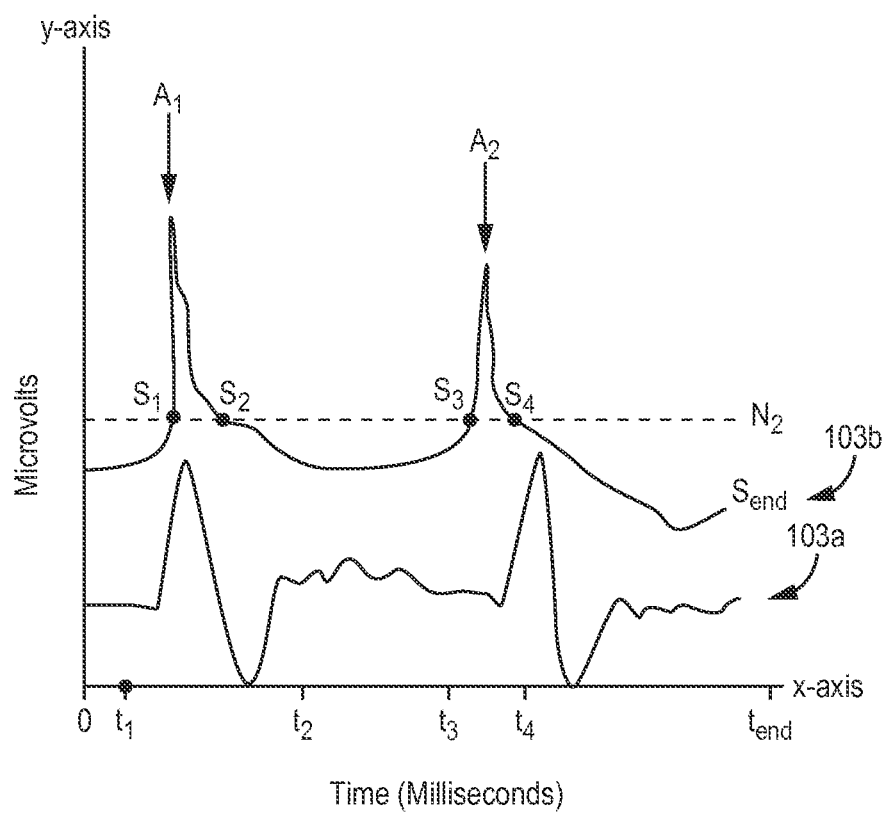
FIG. 20 is a graph compares invalid and valid ECG signals relative to a threshold employed for eliminating invalid signal data.

Block 104 verifies whether the total number $N_1$ of channel data has been processed through method 100. For example, a determination is made as to whether the channel number, presently being processed, is less than the total number $N_1$ of channels. If all of the channel data has been processed, then the present channel number being processed is greater or equal to $N_1$. Therefore, the NO path can be followed to block 106 in which the channel data is completed. In contrast, if the channel number is less than $N_1$, the YES path can be followed from block 104 to block 108 which allows data sampled from the ECG signal to be indexed. Indexed samples means that each sample is assigned a consecutive number relative to the time each sample is located on the signal for that particular channel. The first sample (Sample 1 or $S_1$) is located closest to time zero while the last sample (end Sample or $S_{end}$). For example, 30 samples could be indexed relative to the time each sample appears in the signal. The first sample would be referred to as sample 1 at time 1, sample 2 is at time 2 and so on . . . sample 30 would be at time 30. Exemplary indexed data, sampled from an invalid ECG signal 103b, is depicted in FIG. 20. The data is indexed by sample number relative to time provided along the X-axis shown in FIG. 20. As is further shown, the signal includes two different amplitudes A1, A2.

At block 110, a voltage threshold $N_2$, depicted perpendicular to the Y-axis and horizontal to the X axis in FIG. 20, is used to eliminate or delete indexed samples that may be artifacts at block 112. Artifacts are typically associated with very large voltages but artifacts can also be smaller signals among the noise level.

The elimination process at block 112 begins with setting $N_2$. $N_2$ can be set at $1 \times 10^4$ micro-volts, but the $N_2$ can be set at any number greater than $1 \times 10^4$ micro-volts such as $2 \times 10^4$ micro-volts $3 \times 10^4$ micro-volts, $4 \times 10^4$ micro-volts, $5 \times 10^4$ micro-volts . . . to $10 \times 10^4$ micro-volts. To determine which indexed samples are deleted, all samples that possess a voltage that is at least equal to $N_2$, as is shown in FIG. 20, by four indexed samples $S_1$, $S_2$, $S_3$, and $S_4$ that cross $N_2$. After the samples are located that cross $N_2$, the smallest indexed sample is selected. In the example shown in FIG. 20, the smallest indexed is sample $S_1$. $S_1$ crosses $N_2$ as is indicated by the vertical line that extends from the X-axis through the signal. All indexed samples from $S_1$ to the end of the signal $S_{end}$ at end time point, referred to as $t_{end}$, the windowed ECG signal is deleted. The deleted indexed samples are assumed to include artifacts. An example of an artifact is described with respect to U.S. patent application Ser. No. 14/216,100 dated Mar. 17, 2014, and assigned to the assignee of the present invention, the disclosure of which is incorporated by reference in its entirety herein. Artifacts or pace polarization effects are present on a sensing electrode employed to sense the electrical activity of the heart. While the deleted samples may or may not include artifacts, the process of block 112 substantially ensures artifacts are eliminated. The sample data that remains includes all data that precedes $S_1$. The remaining sample data continues to block 114. With respect to the good ECG signal 103a, $N_2$ does not pass therethrough; therefore, the data from the good ECG signal is not eliminated. FIG. 20 corresponds to block 110 by showing sharp spikes, for example, when the patient's body moves. At decision block 114, method 100 checks for another type of artifact in the sensed signal such as small signals among the noise level. Additionally, at least one cardiac cycle has been sensed by setting the number $N_3$ of samples within a pre-specified time period to an adequately high number of samples (e.g. 200 ms, 175 ms, 150 ms, 125 ms, 100 ms etc.). The samples are searched backwards from the last to the first sample. For example, a determination is made as to whether VALUE (I) minus (−) VALUE (I+$N_3$ (e.g. 200 ms)) is less than $N_4$ (e.g. 10) where $N_4$ checks how the signal changes in magnitude within the 200 samples. N4 can be some other pre-selected number based upon patient specific data. For example, N4 can be set to 30, 20, 15, 10, etc. but is generally less than 30. The range of QRS duration which can be as short as 100 ms but could also be as long as 250 ms. $N_3$ can be set to an integer such as such as 100-250 samples. The sample numbers, provided herein, apply to a sampling rate of 1000 Hz. For different sampling rates, $N_3$ would be different.

If the value (I)−value (I+200) is less than N4 (e.g. 10), then the YES path is followed to block 116 in which a I counter is decreased by 1 which allows the samples to be evaluated from the last sample that was recorded or stored into memory. For example, the counter I is decremented by the equation I=I−1 which allows the samples to be processed from the last sample to the first sample stored into memory. If the VALUE(I)−VALUE (I+$N_3$) is not less than $N_4$ (e.g. 10), then the NO path can be followed from block 114 to block 118.

Figure 5:
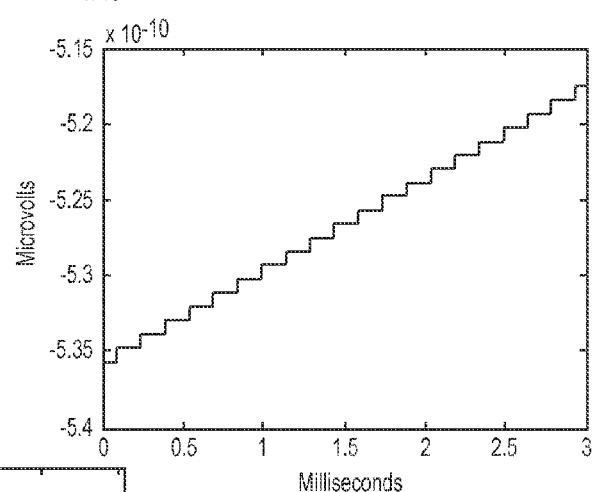
FIG. 5 is a graph illustrating an example linear step function that shows invalid data that is excluded by the method depicted in FIG. 3.
Figure 6:
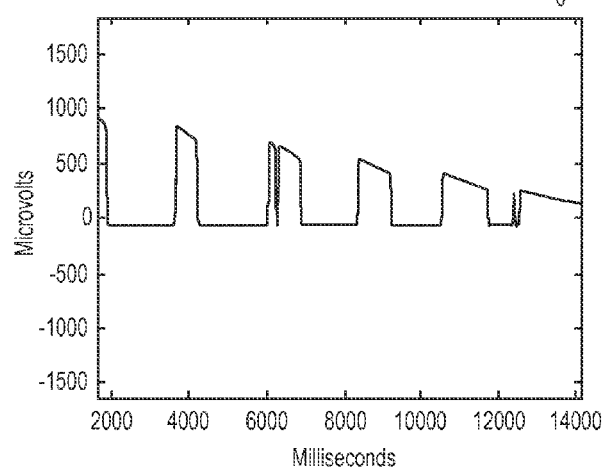
FIG. 6 is a graph illustrating an example of a second derivative of an ECG signal that is not equal to zero.

At block 118, samples from "I", referred to relative to block 116, are deleted to the end. While the samples that remain in block 116 are different from the samples at block 112, the same or similar concept is applied to deleting samples as that which was described relative to FIG. 20, which is incorporated herein. The entire noise signal shown in FIG. 5 is eliminated at block 118 because the magnitude of the change of the signal is very small. The noise signal is a linear step function or considered a flat line. The graph in FIG. 5 ranges from $-5.4\times10^{-10}$ microvolts to $-5.1\times10^{-10}$ microvolts while the X-axis ranges from 0 to 3 milliseconds.

At decision block 120, a determination is made as to whether the samples, that remain after deleting samples at block 118, are greater than a preselected number such as $N_3$. If less than or equal to $N_3$ remain, then the YES path continues to block 134 which causes the data acquired from that channel to be declared invalid. Invalid data from a channel is not a good channel to update onset of QRS wave data. Invalid channel data can be designated by "0" which is distinguished from valid data designated as "1". The designation of channel data as valid or invalid is stored in a data register that is associated with each channel.

If greater than a preselected number $N_3$ of samples remain, the YES path can be followed to block 122. At block 122, the first derivative is determined. The first derivative along with the amplitude of the signal determine whether the signal is sufficiently strong. The first derivative can be determined by calculating the change or delta of the Y-axis divided by the change or delta of the X-axis as to the signal data. At block 124, the second derivative is determined. The second derivative can be calculated by determining the change or delta of two points along the Y-axis divided by the delta of the two points on the X-axis of the Y derivative.

At block 126, a determination is made as to whether the second derivative data is less than $N_5$. $N_5$ is data dependent and is a very small value. For example, $N_5$ can be set at $1\times10^{-6}$ microvolts. Sample data, having second derivative data greater than $N_5$, are kept while the remaining samples are deleted. Specifically, any second derivative data less than or equal to $N_5$ is eliminated from further processing of data. Block 126 eliminates flat-line signals such as that which is shown by an exemplary second derivative of an ECG signal of FIG. 6. If the sample voltage is less than or equal to $N_5$, the process continues to block 128, which relates to determining whether sampled data that has been processed is greater than $X_1\%$ of the total number of samples. $X_1$ can be set at any substantially high percentage of samples that have been processed out of the total number of remaining samples. Exemplary $X_1\%$ can include 80%, 85%, 90% or 95%.

If the sample data being processed indicates greater than $X_1\%$ of the total samples have been processed through method 200, then the YES path continues to block 132 in which the channel data is deemed invalid and the process continues on to block 104. In contrast, if the sample is not greater than $X_1\%$, then the channel data is considered valid. A good channel can be designated by "1" while a bad channel can be designated with a "0" which is stored in the data register and the control logic is returned to block 102.

Method 200, depicted in FIG. 7, determines the channel that is able to acquire the strongest signal or a signal with high fidelity or crispness such as a good amplitude, strong slew rate (i.e. slope of a waveform). More specifically, method 200 checks a signal, beat by beat, from a specific channel to determine whether the signal is adequately strong enough to be used to update onset data. Channels that can be used to update onset data are distinguished from channels that cannot be used to update onset data.

Generally, method 200 assigns a "leadchannel" for each a channel connected to an electrode. Each beat sensed via a channel is assigned a "beat sign" to distinguish beats within a set of beats sensed through the channel. Starting from the first channel, a set of beats are acquired within a pre-specified time frame. Beat information is captured by local maximums. After separating the one-channel signal by beats, local maximums are checked for each beat. Local maximum is a maximum (e.g. amplitude) associated with a beat within a time window.

At block 202, $N_6$ valid channel signals were determined from method 100 and are stored into memory. $N_6$, determined through method 100, can be set to an integer such as 10, 20, 30, 40, 50, 56, 60, 70 etc.

At block 204, a determination is made as to whether a counter, referred to as $I_2$, is less than $N_6+1$. $I_2$ is the number of channels that has been updated in FIG. 7.

If $I_2$ is not less than $N_6+1$, the NO path can be followed from block 204 to block 206, which indicates that data from all of the valid channels have been processed; therefore, the process of checking all channel data is completed. If $I_2$ is less than $N_6+1$, then the YES path can be followed from block 204 to block 208, which requires data to be accessed from memory for that particular channel in order to determine the strength of the slew rate. Data accessed from memory for block 208 was generated from instructions executed in FIG. 10. Block 208 accesses the square of the first derivative data, stored in memory from the execution of instructions described relative from FIG. 10. Exemplary data accessed from memory is the square of the first derivative. The square of the first derivative could have been previously calculated and stored into memory for the signal or the data is calculated after the processor accesses the signal data from memory. Additionally, each local maximum is determined and stored for each beat.

At block 210, a determination is made as to whether a mean of the local maximums beat to beat is greater than $N_8$ such as 200 mV. Typically, $N_8$ can range from about 3.5 mV to about 200 mV. Mean is the average of all of the local maximums within a window. If the mean of the local maximum for each beat is not greater than $N_8$, the NO path can be followed from block 210 to block 214 which indicates that the channel data is valid based on method 100, but the signal acquired from the channel is not strong enough to be used for updating onset data. If the mean of the maximum of each beat is greater than $N_8$, then the YES path can be followed from block 210 to block 212, which requires a determination to be made as to whether the number of sampled beats from a channel is greater than $N_9$ beats (e.g. 50 beats) within a predetermined time period such as 30 seconds. $N_9$ is set to a substantially high number such as 50 beats per 30 seconds compared to a normal heart beat of 30 beats per 30 seconds. A substantially high number of beats within 30 seconds causes the YES path to be followed to block 214, which indicates that particular channel data is considered valid but is not strong enough to be used for updating onset data If the number of beats per 30 seconds is not greater than $N_9$ beats, then the NO path can be followed from block 214 to block 216, which sets a beat counter, referred to as BEAT, equal to 1.

Figure 8:
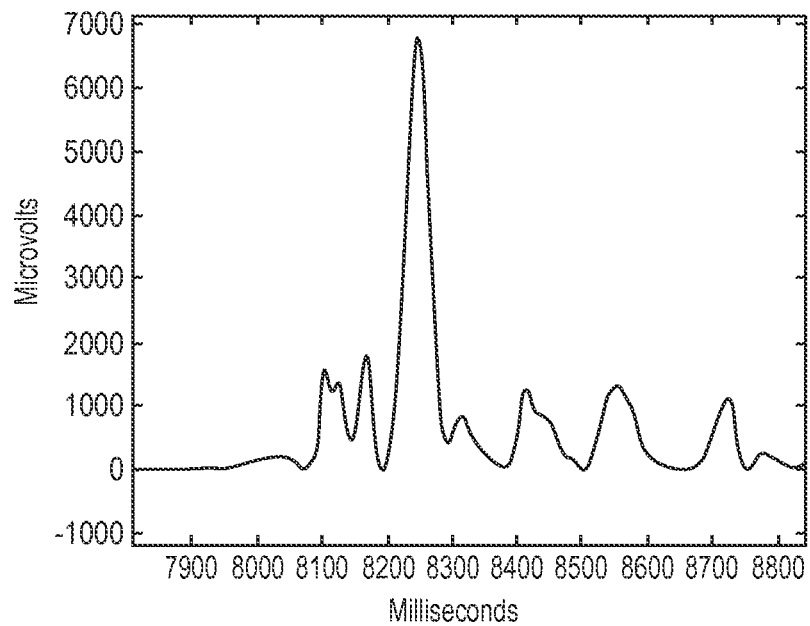
FIG. 8 is a graph illustrating an example rectified ECG that shows onset of a local depolarization waves determined by the method depicted in FIG. 7.

Block 218, requires the processor to store and/or acquire from memory, beat to beat data that is compared to M. For example, local maximum information corresponding to each beat for a channel signal is stored into memory. Thereafter, block 218 determines whether all of the beat and local maximum data has been processed and stored into memory. Exemplary local maximum data within one beat is shown in the window of FIG. 8 while FIG. 9 displays two different local maximums corresponding with two different beats within a time window. To determine whether all beat and local maximum information has been processed and stored into memory, block 218 requires a determination be made as to whether BEAT<M where BEAT is the number associated with the beat data that is being processed or has been last processed while M is the last beat number or the total number of beats.

According to block 218, if BEAT<M, the YES path indicates that all of the beat and local maximum data has been processed and stored into memory. The YES path from block 218 can be followed to decision block 220. At block 220, a determination is made as to whether the beat to beat data stored in memory indicates greater than a preselected percentage $X_2\%$ (e.g. 75%, 80%, 85%, 90%, 95% etc.) of beat data is considered valid. If greater than, for example, 75% of beat data for a particular channel is considered valid, then that channel is deemed valid at block 222 and the channel can be used to update the onset on a one time only basis or on a continuous basis. In contrast, at block 220, if the beat to beat data stored in memory indicates equal to or less than a preselected percentage of (e.g. 75%, 80%, 85%, 90%, 95% etc.) beat data is considered valid, then the data acquired from that particular channel is considered valid but not sufficiently strong at block 214 and will not be used to update the onset data.

Returning to block 218, if BEAT is not less than M (i.e. last beat number or the total number of beats) the NO path to block 224 indicates that the beat data is still being processed and stored into memory.

Each beat is checked to determine how many local maximum in each beat is larger than 10% of the mean at block 210. After a determination is made as to whether any local maximums exist over 10% of the mean of the local maximums for each beat are present, the number of local maximums, if any, over 10% are stored into memory (e.g. memory of the programmer).

After acquiring information for each beat, blocks 225-230 determine how many local maximums are within a designated region. For example, at block 225, if there is one local maximum within a window, then the YES path can be followed to block 232. At block 232, after deleting the present maximum value within the window, any remaining local maximums are located and counted that are within the window.

At block 234, a determination is made as to whether greater than two local maximums are within $X_3\%$ (e.g. 90% etc.) of the maximum amplitude of the remaining local maximums. Essentially, block 234 determines which local maximum is the largest within the window and then also determines whether greater than two local maximums are within $X_5\%$ (e.g. 90% etc.) of the maximum amplitude of the signal. If there are greater than two local maximums, the beat counter is set equal to zero at block 236. The beat counter is incremented by 1 through the equation BEAT=BEAT+1 at block 238. Thereafter, the process continues to block 218.

Returning to block 225, the NO path indicates that the beat data has been processed and can now be classified with respect to detection of beats per window at blocks 226, 228, and 230. Decision block 226 determines whether two local maximums are present in a window. If so, then the YES path can be followed from block 226 continues to decision block 242 in which another determination is made as to whether a minimum between the present two local maximums is less than a preselected percentage $X_4\%$ (e.g. 5%) of the local maximum.

The NO path can be followed from block 242 to block 236 in which BEAT counter is set equal to zero. In contrast, the YES path can be followed from block 242 to block 240 in which the BEAT is set equal to one. Thereafter, the BEAT counter is incremented at block 238 and then the process continues at block 218.

Returning to block 226, the NO path continues to block 228 in which a determination is made as to whether three local maximums are located and counted within a window. If so, then the YES path continues to decision block 244. At block 244, the value of the smallest local maximum within a window is determined. It is then determined whether more local maximums within a window are within a preselected percentage of the value of the smallest local maximum. Through the comparison, a determination can be made as to whether the local maximum is within the preselected percentage of the smallest local maximum within a window. The YES path can be followed from block 244 to block 236 in which the BEAT counter is set equal to zero. The NO path can be followed from block 244 to block 240 in which the BEAT counter is set equal to one.

The NO path from block 228 continues to block 230 in which a determination is made as whether four local maximums within a window then the process continues to block 236 in which the BEAT counter is equal zero. In contrast, the NO path can be followed from block 244 continues to block 240 which causes BEAT=1.

Data, stored into memory as a result of execution of computer instructions generally depicted in FIG. 7, is used to initialize parameters associated with FIG. 10. However, skilled artisans will appreciate that step 208 of FIG. 7 accesses data from memory that is acquired from execution of instructions generally embodied in FIG. 10. In one or more embodiments, step 208 serves as a call function to execute a subroutine (e.g. first derivative etc.) and store the data resulting from the subroutine into memory.

Figure 23:
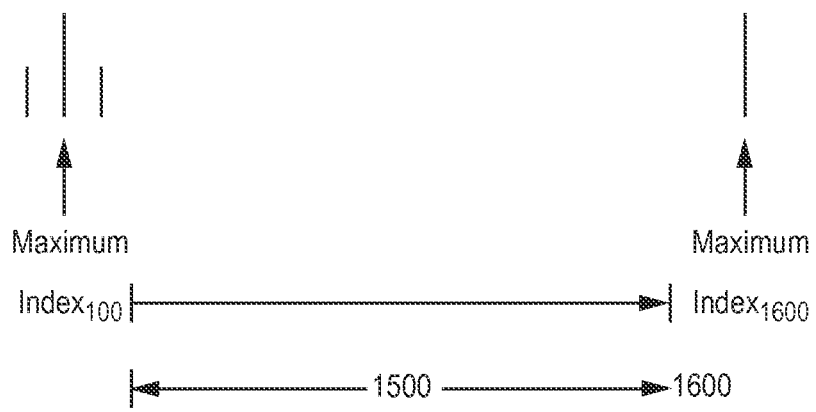
FIG. 23 is a schematic diagram depicting time index samples of local maximums.

Method 300, depicted in FIG. 10, ensures that only the most accurate signal data is used to calculate the onset depolarization data. In particular, method 300 determines the beat information. The beat information is acquired and stored into memory through FIG. 10 before the onset is updated for each beat. For example, method 300 determines a maximum for each beat that is acquired from a signal on a channel to ensure only the most accurate onset depolarization data is obtained. Method 300 further eliminates unnecessary artifacts that may be found in the signal while also ensuring that beats are not missed. Essentially, a determination is made as to how separated in time the local maximums are to each other, as is shown in FIG. 23. For example, assume one time index sample is 100 while another shown at time index sample is 1600. A set of local maximum is shown at time index sample 100 while only one local maximum is shown at time index sample 1600. The difference between the two time index samples is 1500, which indicates how separated in time the local maximums are to each other.

In order to eliminate unnecessary artifacts and/or ensure beats are not missed, a ratio value R is adjusted in method 300. For example, if the difference of the time sample indexes of the neighboring local maximum is larger than $N_{10}$ (e.g. sample index 1500) then beats were missed or skipped. In order not to skip beats, the ratio value R is decreased to obtain a new R so that beats are not skipped. Additionally or alternatively, if the difference of the indexes of the neighboring local maximum is smaller than $N_{11}$ (e.g. sample index 400). unnecessary artifacts are found between two beats. In order to eliminate unnecessary artifacts, the ratio value is increased to a new R at block 326.

Method 300 begins at block 302 in which a series of calculations are performed. For example, the first derivative can be calculated, as previously described or through any other suitable method. The square of the first derivative is then determined.

Figure 11:
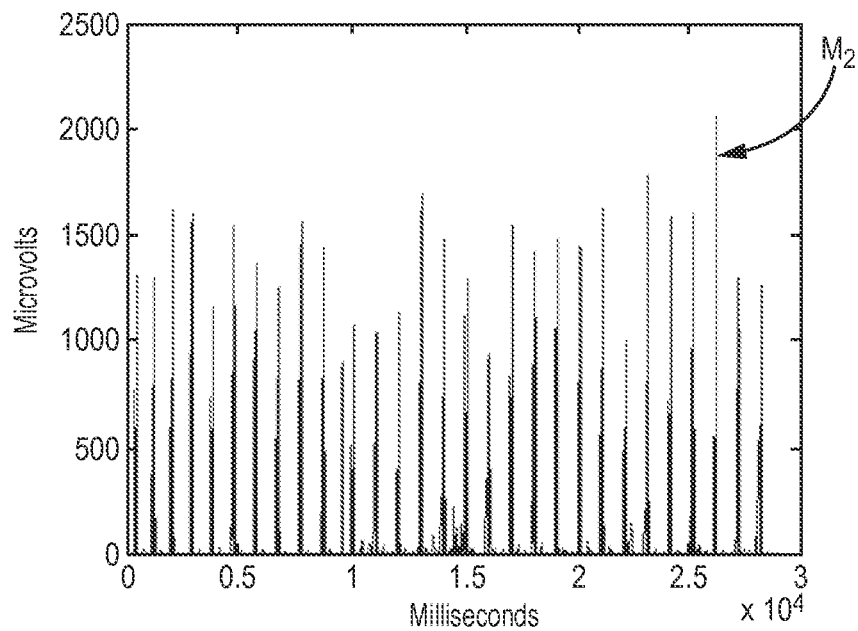
FIG. 11 is a graph illustrating a square of a first derivative of an ECG signal that shows a set of local maximums associated with a set of beats.

Block 304 ensures every signal datum are computed. For example, a determination is made as to whether I<$N_9$, in which $N_9$ was previously defined. The NO path can be followed from block 304 to block 312 in which the second derivative is calculated as previously described or through any other suitable method. The YES path from block 304 continues to block 306 in which another determination is made as to whether the square of the first derivative value is greater than R*$M_2$ where R is a ratio value (e.g. 0.10) can be selected as any other number based on data statistics. $M_2$, shown in FIG. 11, is considered the maximum amplitude of the entire ECG signal shown in a time window that extends up to $3\times10^4$ milliseconds.

Figure 12:
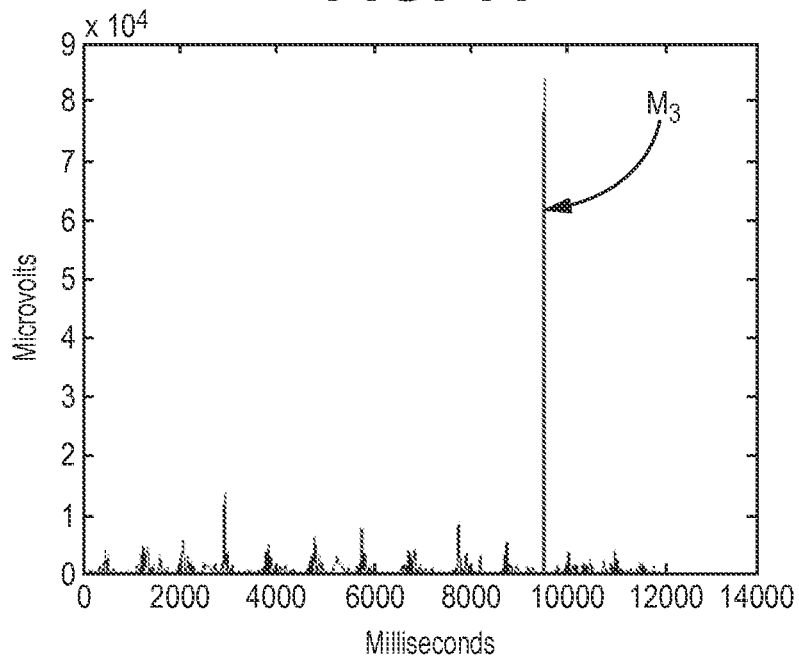
FIG. 12 is a graph illustrating a square of a first derivative of another exemplary ECG signal that shows a set of local maximums associated with a set of beats.

For signals that are similar to the signal depicted in FIG. 12, one local maximum is much larger than the rest. In this situation, information could be missed for numerous beats. Therefore, the algorithm checks to see if the maximum (i.e. M3) of those local maximums are much larger than the mean. For signals like FIG. 12, the maximum M3 will definitely be much larger than the mean. Therefore, the algorithm deletes the maximum M3 and repeats method 300 to get the beat information.

The YES path from block 306 continues to block 310 in which the counter I is incremented by 1 and the process continues to block 304. The NO path from block 306 continues to block 308 in which the differential equation is set equal to zero. Setting the differential equation equal to zero locates the critical points such as local maximums and minimums, referred to as local extrema, on a function's graph. Local extrema occur at critical points of the function such as where the derivative is zero or undefined.

Returning to block 312, after the second derivative has been calculated, the local maximums within a window can be determined at block 316. The second derivative test can be used to find critical points such as local maximums or minimums. The local maximums are found by using the sign of the second derivative. The sign of the second derivative test is provide as follows:

If df/dx (p)=0 and d2f/dx2 (p)<0, and d2f/dx2(p+1)>0 then f(x) has a local minimum at x=p.

If df/dx (p)=0 and df/dx (p)>0, and df/dx(p+1)<0 then f(x) has a local maximum at x=p.

Figure 9:
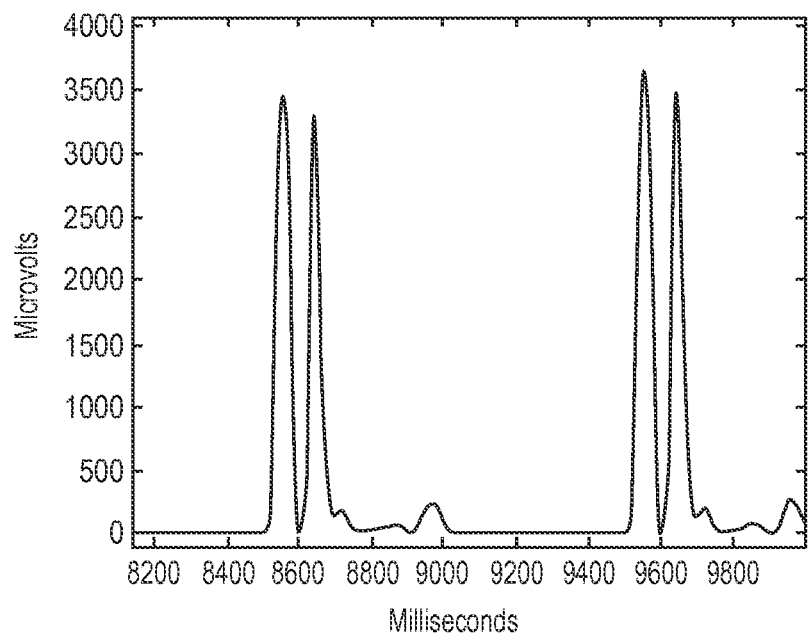
FIG. 9 is a graph illustrating an example of a rectified ECG that shows onset of two different local depolarization waves determined by the method depicted in FIG. 7.

Rectified signals, shown in the FIGS. 8-9, depict critical points (e.g. local maximums) in a single direction, to ease the physicians reading of the signal.

Figure 35:
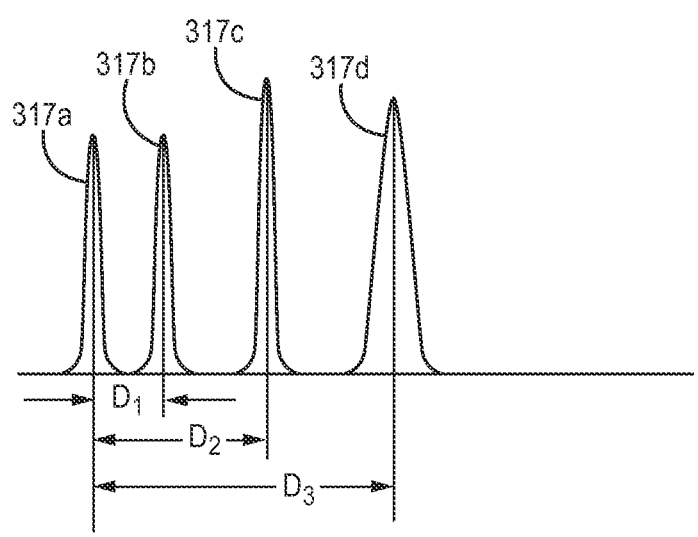
FIG. 35 depicts first local maximums amongst a set of local maximums.

At block 316, a determination is made as to whether local maximums exist within a window. The NO path from block 316 continues to block 318 in which the channel is considered a bad channel or an unacceptable channel from which to update onset data. A channel designated as a bad channel is stored into memory and will not be used to update the onset. The YES path from block 316 continues to block 320. At block 320, the second derivative is calculated as previously described and stored into memory. At block 322, the index of the first local maximum of a preselected number of samples is stored into memory. Exemplary first local maximum 317d is shown in FIG. 35. FIG. 35 depicts a group of local maximums associated with an ECG signal acquired from an unipolar electrode. Starting from local maximum 317a, a determination is made as to the distance (D1) to the next local maximum 317b. If the distance (D1) is too small (i.e. smaller than a threshold) then local maximums 317a,b are counted as one or less than one beat. The minimum time threshold between each beat can depends on each patient. An exemplary threshold could be based upon the threshold that is reliant on the sampling frequency (e.g. 200 samples is 1 heart beat etc.) which is dependent upon the machine employed for performing the present disclosure. Exemplary sampling frequencies for the machines implementing methods 100-300 may range from 100 to 1000 Hertz. The threshold can be customized for each patient and inputted by the user. Additionally, local maximum data 317b is not being recorded. A determination is then made as to the distance (D2) between local maximum 317a to the local maximum 317c. If the distance (D2) is still too small (i.e. smaller than a threshold) then local maximums 317a,b,c are counted as one or less than one beat and local maximum data 317c is not recorded as a first local maximum. Yet another determination is made as to the distance (D3) from local maximum 317a to the local maximum 317d. If the distance (D3) is greater or equal to the threshold indicative of a new heart beat, then local maximum 317d is determined to be the first local maximum. The first local maximum for the new beat is stored into memory.

At block 324, a determination is made as to whether a difference from an index of one local maximum to another is larger than $N_{10}$ or smaller than N11. The NO path from block 324 continues to block 328 whereas the YES path continues to block 326.

At block 326, the ratio is changed. The ratio is changed if the difference of the indexes of the neighboring local maximum is larger than N10, as shown in FIG. 11. A difference of the indexes of the neighboring local maximum larger than $N_{10}$ means some beats may have been missed, as shown in FIG. 12 in which the local maximums are too far apart. Therefore, the ratio value must be decreased. For example, the ratio can be set to 7.5% or R=0.075. In contrast, if the difference of the indexes of the neighboring local maximum is smaller than $N_{11}$, then artifacts may be located between two beats. Therefore, the ratio value must be increased to address skipped beats as shown in FIG. 12. For example, the ratio can be 12.5% or R=0.125.

At block 328, the local maximum in each beat is located using the newly modified ratio. The local maximums are found by determining the first derivative of the ECG signal, as previously explained. At block 330, the mean of local maximums in a beat are determined. The mean is obtained by adding local maximum values together and dividing by the number of local maximums within the time window.

At block 332, local maximum(s) larger than twice the mean is deleted or eliminated since the much larger local maximums are likely to be an artifact. Referring to FIG. 12, the local maximum designated as M3 is clearly twice as large as the mean of local maximums. At block 334, the mean of the remaining local maximums is calculated.

At block 336, a determination is made as to whether a first loop had occurred. The NO path from block 336 continues to block 338 and the process is stopped. The YES path from block 336 returns to block 302. After the computer instructions for FIG. 10 are completed. After determining which lead is sufficiently adequate to update onset data, onset of data can be determined for each beat.

Figure 14:
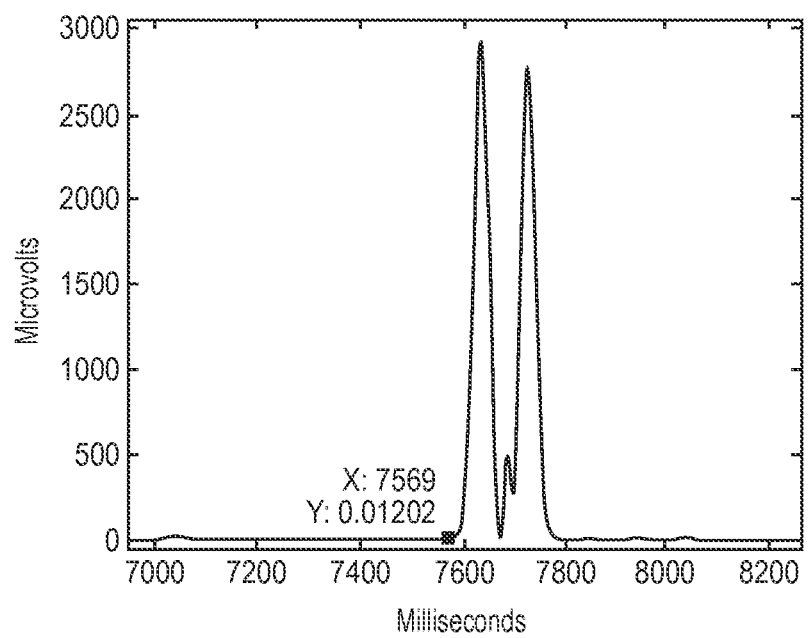
FIG. 14 is a graph diagram of an example two different local maximums in which the onset of heart depolarization has been determined after performing methods 100-300 depicted in FIGS. 3, 7 and 10.
Figure 24:
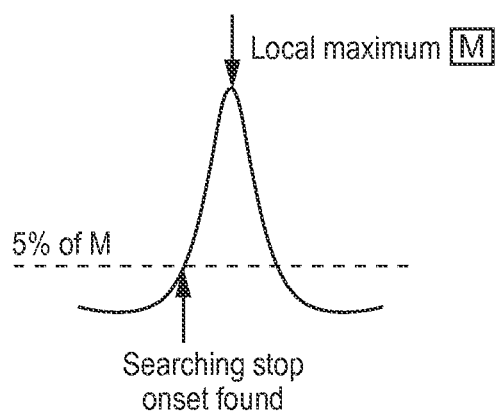
FIG. 24 depicts an acceptable onset of cardiac depolarization such that the square of the first derivative is smaller than 5% of the first local maximum that was updated in FIG. 10.

For each beat, the process starts from the first local maximum which is updated by the methods described herein. The data is searched backwards until the square of first derivative is smaller than a pre-specified number (e.g. 10% or less 8% or less, 6% or less, 5% or less, 4% or less, or 2% or less) of the first local maximum associated with a particular beat, such as the first local maximum 317d depicted in FIG. 35. For example, for each beat, start from the first local maximum which is updated in FIG. 10 and search backwards until the square of first derivative is smaller than a preselected percentage (e.g. 5% etc.) of this local maximum (i.e. first local maximum). The onset is smaller than 5% of this local maximum M, as shown in FIG. 24. Local maximum M is generated from instructions executed in FIG. 10. FIG. 24 demonstrates the last step which is updating the onset. FIGS. 13-14 provide exemplary data as to FIG. 24. FIG. 13 is an ECG signal in which the onset is detected at the point x=7569. FIG. 14 is the square of the first derivative of the ECG signal. It uses the algorithm shown in FIG. 24, searching backwards from the first local maximum until the square of first derivative is smaller than a preselected percentage (e.g. 5% etc.) of this local maximum (i.e. first local maximum) which is x=7569. FIGS. 13 and 14 demonstrate the algorithm, graphically represented in FIG. 24, is correct.

Once the square of first derivative is smaller than 5% of the first local maximum, a determination is made that the onset of depolarization has been found and further searching for the onset is terminated. The onset of depolarization is set equal to the square of the first derivative that is less than the pre-selected percentage of the first local maximum. Once the onset of depolarization of the ECG has been found, the onset of depolarization is updated (e.g. stored in the memory of the programmer) in the system, which will increase the accuracy for determining the activation time calculation and distribution display. In one or more embodiments, the onset of cardiac depolarization is determined solely using implantable electrodes. The IMD is then updated with a more accurate onset of cardiac depolarization. Therefore, accurate onset data helps a physician to make the best decisions in choosing the proper treatment for the patients.

Exemplary instructions for one or more embodiments of the entire algorithm are presented below.

1. Identify valid channels and eliminate invalid channels as shown and described relative to FIG. 3. Keep the valid channels. Assign a name such as "channelsign" to each channel.
    a. Start from the first channel (box 104).
    b. Start from the last sample for a particular channel, search for the indexes until the value of the sample is smaller than threshold level such as $1 \times 10^4$ microvolts. Thereafter, eliminate samples from the smallest indexed sample to the end (box 112).
    c. Continue searching backwards (i.e. last sample to first sample). If the value change is less than 10 within 200 samples (i.e. 10 checks how the signal changes in magnitude within the 200 samples), continue until larger than 10, and delete those samples until the end (box 112, 114).
    d. Then determine if more than 200 samples are still left (box 114). If not, set channelsign to 0 and stop.
    e. If larger than 200 samples, calculate the second derivative of the signal (boxes 122, 124). Search from the last sample until the second derivative is larger than $10^{-6}$ microvolts (box 126) and record the number of samples. If the number is larger than 90% of the number of all samples, set channelsign to 0. Otherwise, set channelsign to 1.
2. The channel number is increased by one. Determine whether the channel number is larger than the total number of channels (i.e. 56) being processed (box 104). If yes, stop (box 106). Otherwise, go to step b.
3. Referring to FIG. 7, select proper channels (i.e. channels that remain after execution of instructions from FIG. 3) that can be used to update the onset data. For the remaining channels, find those channels that are proper to update the onset. Assign a "leadsign" to each channel. For each channel, assign a "beatsign" to each beat.
    a. Start from the first channel and find how many beats are in this data set.
    b. If the mean (box 210) of the maximums for each beat is less than 200, then the channel is not used to update onset. Go to step f.
    c. If there is more than 50 beats found (box 212), then the channel is not used to update onset. Go to step f.
    d. Check through each beat. Find how many local maximum in each beat are larger than 10% of the mean (210).
    If the number is 1 (box 225), delete this local maximum and find the local maximum after the elimination of this local maximum. If more than or equal to three local maximums are larger than the 90% of the maximum of the remaining data in this beat, assign beatsign as 0; otherwise, beatsign will be 1.
    If the number is 2 (box 226), check if the minimum between these two local maximums is less than pre-selected amount (e.g. 5%) of the maximum. If yes, assign beatsign as 1, otherwise beatsign=0.
    If the number is larger than or equal to 4 (box 230), assign beatsign as 0.
    If the number is 3 (box 228), find the value of the smallest local maximum and search to see if there are a fourth or even more local maximums those values are within 80% of the smallest local maximum value. If yes, beatsign is set to 0. Otherwise, beatsign is set to 1.
    e. If more than 75% of the beatsign are 1, then the lead can be used and assign leadsign as 1 for this lead (box 220). Otherwise, assign leadsign as 0.
    f. Go to the next valid channel. Check if the channel being processed is the last one of the total number of channels being processed. If yes, stop. Otherwise go to step b.
4. FIG. 10 updates and stores the beat information by finding how many beats are in this data set. The result from FIG. 10 is accessed by FIG. 7 operations. The first maximum is located which is larger than 10% of the mean of maximums for each beat.
    a. Calculate the square of the first derivative of the signal (box 302).
    b. Find samples that are larger than 10% of the maximum of square of first derivative (box 306). Those smaller ones are set to zero and assigned to another matrix.
    c. Find the second derivative of these samples (box 312). Use the first derivative to find local maximums (box 314). If no local maximum exists (box 318), give a sign to the function "isgoodlead" to set leadsign for this channel as 0, and stop.
    d. Set the indexes of those local maximum to the same values if they are within 500 samples. After "unique" command, the rest are the indexes of the first local maximum in each beat.
    e. If the difference of these indexes are larger or smaller than 1500 or 400, change the ratio to 7.5% or 12.5% and re-process (box 324).
    f. After that, find the maximum in each beat. The maximum in each beat is not the value of the first local maximum. Calculate mean of these maximums. Delete maximums which are larger than twice of the mean (box 332). Recalculate the mean (box 334). Also, use the recalculated mean as the criterion, instead of the maximum of the first derivative, and re-do the procedure from step b (box 336).
5. Update onset data.
    For each beat, start from the first local maximum, which is updated in step 3, and search backwards until the square of first derivative data is smaller than 5% of this first local maximum. FIG. 35 and the accompanying text describe the manner in which the first local maximum is located for each beat and then stored in memory. The first derivative data that is smaller than a user inputted percentage (preselected percentage e.g. 5% or less, 4% or less, 3% or less, 2% or less, 1% or less etc.) of this first local maximum for a beat is considered to be the onset of depolarization. Onset data is updated for each beat. After the onset data has been updated, the signal can undergo further signal processing. For example, method 1200 depicted in FIG. 25 and/or method 1300 depicted in FIG. 29 can be used to further improve upon the onset data obtained from methods 100-300. Method 1200 determines whether a signal, acquired from a channel of a multichannel mapping system, is valid or is invalid due to artifacts. In particular, method 1200 determines whether a beat, within a window that extends up to 200 ms, is a valid QRS wave.

Method 1200 begins at block 1202 in which the onset of the depolarization is updated, as described herein with respect to methods 100-300. At block 1204, a determination is made as to whether each channel connected to an electrode has had its signal processed. The total number of channels used in method 1200 is automatically preset or set by the user and stored into memory. For the sake of illustration, in one example, the total number of channels, from which time sampled signal data is acquired, is set to N1 (e.g. 55). In one or more embodiments, a preferred range of 30 to 50 channels are employed. Additionally, method 1200 requires a counter to be automatically initialized by setting the counter to a preselected value (e.g. set to 0, etc.) that allows each channel to be counted in order to ensure data, from each channel, is processed. The NO path from 1204 continues to block 1220 which indicates all channels have finished being processed through method 1200 and are deemed to acquire either valid or invalid signals. The YES path from block 1204 indicates that a channel still must undergo method 1200 operations and therefore continues to block 1206.

Figure 26:
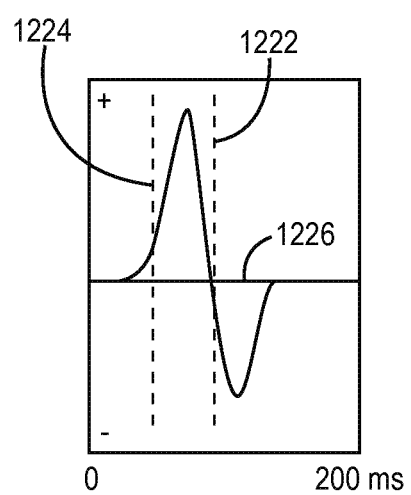
FIG. 26 graphically depicts an exemplary derivative of a signal.

At block 1206, a first derivative is calculated from a signal acquired from an electrode (e.g. surface electrode etc.) and stored into memory. FIG. 26 depicts an exemplary first derivative of a signal. The maximum of the first derivative 1224 depends on the detected onset of the acquired signal. The maximum of the first derivative 1224 exhibits a positive slope along the dashed line since the curve rises. The minimum of the first derivative 1222 exhibits a negative slope at the dashed line. The ending of the minimum of the first derivative 1222 depends on the size of the time window. Baseline 1226 is displayed merely to provide context to the first derivative of the signal within the window.

Figure 27:
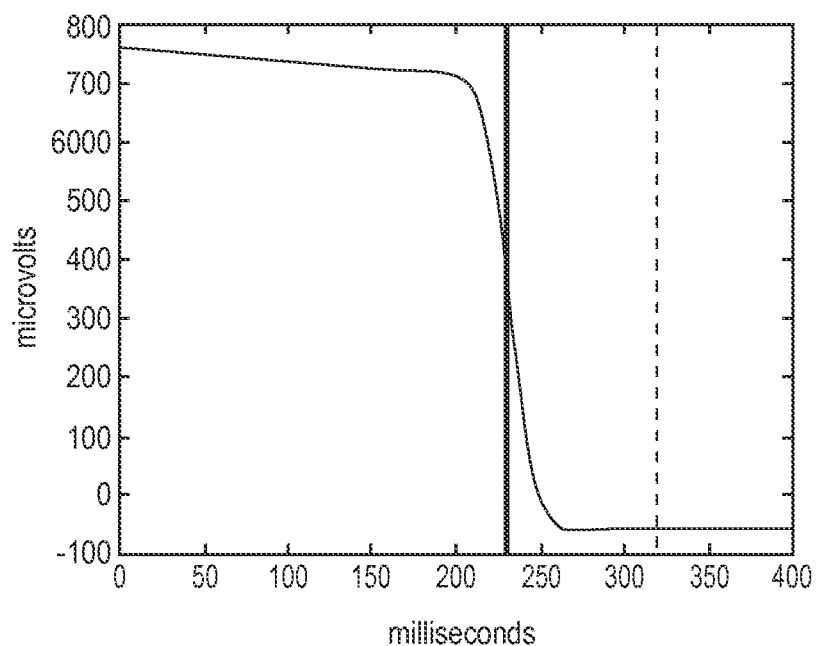
FIG. 27 graphically depicts an exemplary derivative of an artifact signal.
Figure 28A:
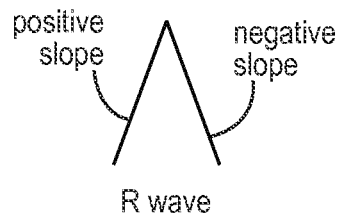
FIG. 28A graphically depicts a R waveform.
Figure 28B:
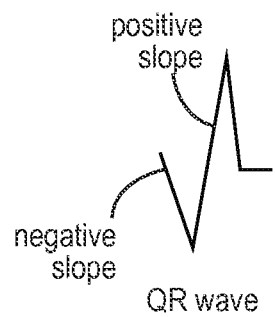
FIG. 28B graphically depicts a biphasic QRS waveform.
Figure 28C:
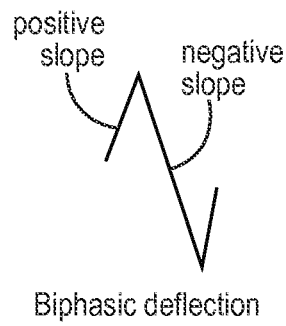
FIG. 28C graphically depicts a R-s waveform.
Figure 28D:
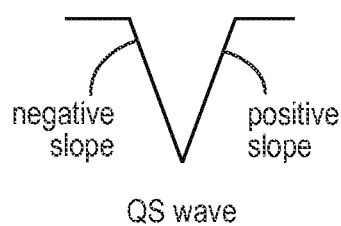
FIG. 28D graphically depicts a QS waveform.

At block 1208, a determination is made as to whether the signs are different for the waveform. If the signs are the same, the NO path continues to block 1216 where the signal is declared invalid. If the signs are different, the YES path from block 1208 continues to block 1210. Different signs are shown by the exemplary waveform depicted in FIG. 26. The minimum of the first derivative shown in FIG. 26 possesses a negative sign. The maximum of the first derivative 1224 shown in FIG. 26 possesses a positive sign. FIGS. 28A-D provide several other exemplary waveforms that exhibit a positive and negative slopes. For example, FIG. 28A is a typical R waveform, FIG. 28B is a biphasic QRS waveform, FIG. 28C is a R-s waveform, and FIG. 28D depicts a QS waveform. A valid R wave exhibits a minimum of the first derivative in which the curve exhibits a downward or negative slope and a maximum derivative that exhibits a rising or positive slope, and a ratio that is close to each other. In contrast, the waveform in FIG. 27 is an artifact signal in which the maximum (positive) and minimum (negative) slopes are indicated by the dashed black and solid black lines respectively. The maximum positive slope has value of 0.00002 microvolts/ms and the minimum negative slope has value of −17.6 microvolts/ms.

At block 1210, a ratio is calculated of the absolute value taken of the larger one of derivatives in the numerator over the smaller one of the derivatives in the denominator. Accordingly, the magnitude of the maximum and minimum of the derivative determine the numerator and denominator for the ratio calculation. An exemplary ratio calculation can be shown with respect to FIG. 27. Taking the ratio of the magnitudes, the ratio value is 17.6/0.00002=8,80,000 which is a large number and indicates that the signal is not a physiologically valid signal, rather, the signal is an artifact. If the signs are the same for each slope, then artifacts have been confirmed to have been detected and the signal acquired from the channel is deemed invalid at block 1216.

At block 1212, a determination is made as to whether the ratio calculated at block 1210 is greater than a preselected number C (e.g. 5). C can range from 2 to 12. If the ratio is not greater than the preselected number C from block 1208, then the NO path from block 1212 continues to block 1214 in which the signal acquired from a channel is considered valid. If the ratio is greater than the preselected number from block 1210, then the NO path from block 1212 to block 1214 indicates the signal is considered valid.

Signals from blocks 1214 and 1216 continue to block 1218. At block 1218, the channel number counter is increased by 1 then checked at block 1204 to ensure all of the channels are processed. Blocks 1202-1212 are repeatedly performed until each channel of the total channels N1 are completed. Skilled artisans understand that method 100 and/or method 1200 can be applied to any signal to eliminate artifacts. For example, methods 100 and 1200 can also be used with any physiological signal (e.g. cardiac signal, neural signal etc.) acquired from the body of the patient using surface electrodes and/or implanted electrodes.

In addition to eliminating artifacts, other embodiments of the present disclosure can be implemented to determine whether an ambiguous signal is being detected from an electrode during any activation mapping used in a variety of electrophysiologic procedures. Activation mapping can involve mapping directly from the surface of the heart, from within the cavity of the heart or from the body belt developed for cardiac resynchronization. Other examples may include multi-electrode arrays (e.g. constellation baskets) in combination with a catheter that can then be deployed in the intracardiac space for simultaneous or sequential mapping of electrical activity of the heart surface using surface electrodes. FIG. 29 depicts method 1300 for identifying ambiguous cardiac signals during electrophysiologic mapping. Ambiguous signals may occur during atrial fibrillation (AF) mapping and/or an electrode being placed near or in a poor substrate (e.g. scar tissue). Ambiguous cardiac unipolar signals can exhibit a morphology with multiple negative slopes of comparable magnitudes within a single window, thereby making it difficult to identify the activation-time uniquely acquired from that electrode. Method 1300 detects such ambiguous signals, and automatically "edits" the activation times corresponding to those electrodes based on activation times from neighboring electrodes with non-ambiguous signals. Method 1300 essentially uses activation times from neighboring electrodes to determine the correct activation time in response to determining ambiguous signals are being acquired from an electrode. Acquiring activation times using surface electrodes is described in U.S. patent application Ser. No. 14/227,919 to Ghosh et al., filed on Mar. 27, 2014 and 61/817,240 filed on Apr. 30, 2013 and is entitled, SYSTEMS, METHODS, AND INTERFACES FOR IDENTIFYING OPTIMAL ELECTRICAL VECTORS" and is incorporated herein by reference in its entirety.

Skilled artisans will appreciate that method 1300 can be applied to any biosensed signals. For example, method 1300 can be applied to electrical signals acquired from an electrode apparatus described herein and/or electrodes implanted in the patient's body and/or subcutaneous electrodes. Method 1300 also can be applied to a constellation or basket. Method 1300 can also be applied to a balloon on a delivery tool or catheter. Additionally, method 1300 can be implemented using a moving probe.

The data, generated by implementing blocks 1302-1310, are previously described herein and incorporated by reference in their entirety. The data is automatically stored in memory immediately after being generated. Computer instructions e.g. firmware can be used to automatically store data generated from any one of the blocks in any of the flow diagrams presented herein.

Figure 30:
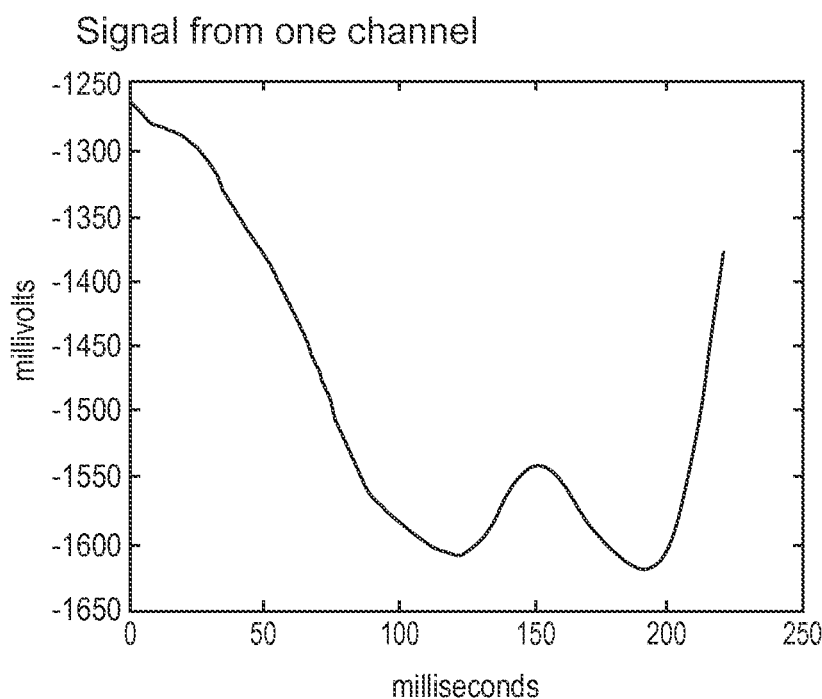
FIG. 30 depicts an ECG signal acquired from a surface electrode associated with an electrode apparatus.
Figure 31:
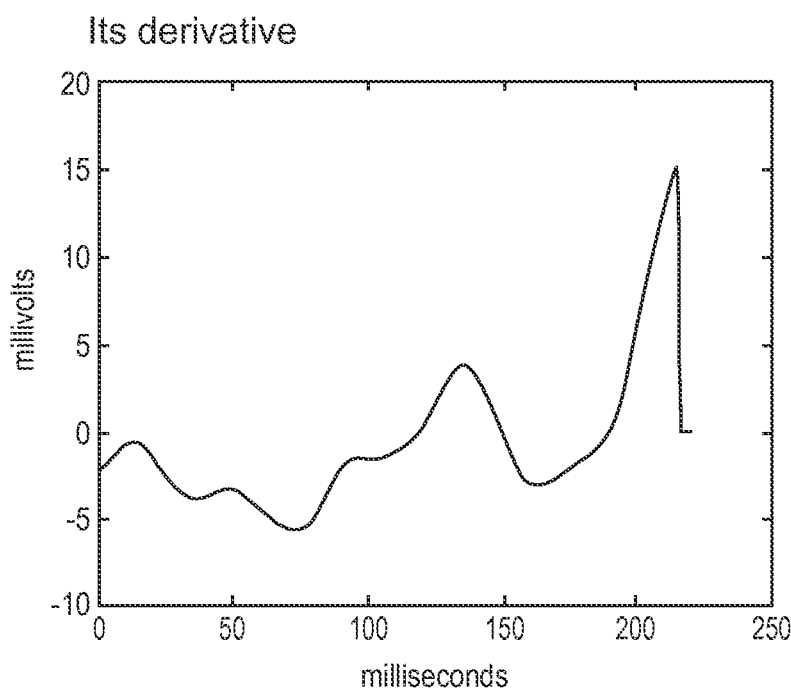
FIG. 31 depicts a derivative of the ECG signal from FIG. 30.
Figure 32:
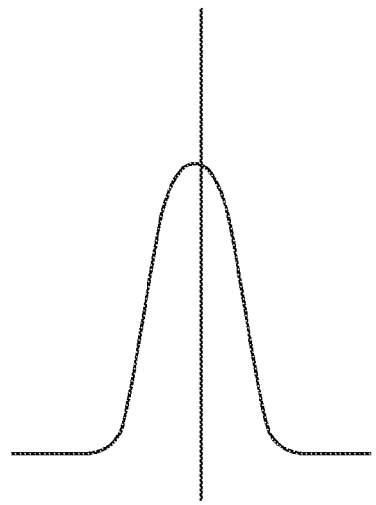
FIGS. 32 and 33 show exemplary signals with dashed lines intersecting at a steepest point of each curve.
Figure 33:
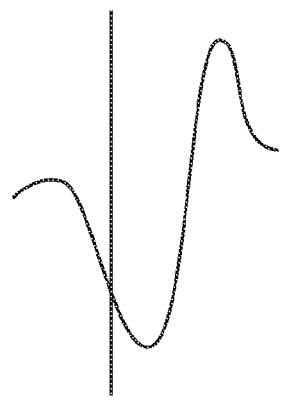

Method 1300 begins at block 1302 in which the onset data is determined and stored into memory. Onset data can be obtained from FIGS. 3, 7 and 10 or acquired from the sensed signal. At block 1304, the first derivative is calculated of a signal, as previously described, and stored into memory. An exemplary ECG signal is shown in FIG. 30 with its corresponding first derivative curve shown in FIG. 31. The first derivative is used to identify the timing of a steepest negative slope of the signal for determining the activation time corresponding to a particular electrode. The signal can be acquired from one or more electrodes disposed on the surface of the heart, from within the cavity of the heart, or from the body surface using surface electrodes. FIGS. 32 and 33 show exemplary signals with dashed lines intersecting at the steepest point of each curve.

At block 1306, the local maximum and local minimums are located within a window using know techniques. One exemplary technique involves comparing one point to another point along the curve until all the points along the curve have been processed. The technique may include a sorting operation and/or swapping operation to determine minimum and maximum derivative data points. For example, two of the largest local minimum in a window should have at least one local maximum therebetween. Derivative data for local maximums and local minimums is helpful to define regions since first derivative maximums and minimum should be zero.

At block 1308, the value of minimum of the first derivative and its corresponding time index in each region is recorded. The time index relates to the indexed sample as described relative to FIG. 20. Minimum derivative and its corresponding time index in each region is shown and described in method 100 and is incorporated by reference herein.

At block 1308, two minimum derivatives are located within a window extending a pre-specified time period (e.g. 200 ms). The two minimum derivatives having the largest magnitudes (i.e. absolute values) among a set of minimum derivatives are located within the window. Sorting and/or swapping operations may be used to determine two minimum derivatives.

At block 1312, a ratio is calculated. The ratio uses the following formula:

ratio=abs(larger one of the minimum derivatives)/abs (smaller one of the minimum derivatives) where "abs" represents the absolute value.

Additionally, the timing difference ("dis") between the absolute ("abs") value of the difference between a first and second index are calculated using the following equation where index1 and index 2 are the time indices corresponding to the two minimum derivatives:

dis=abs(index1−index2)

where index1 relates to the derivative data with the larger magnitude (i.e. "larger one" block 1210 FIG. 25) and index2 relates to the derivative data with the smaller magnitude (i.e. "smaller one" block 1210 FIG. 25).

At decision block 1314, a determination is made as to whether the distance between the two indices is less than a pre-selected number such as 10 ms. The pre-selected number is typically in a range of about 5 to about 15 ms. The YES path from block 1314 continues to block 1316 which indicates the signal is valid. The process is completed or finished at block 1322. The NO path from block 1314 continues to decision block 1318.

Figure 34:
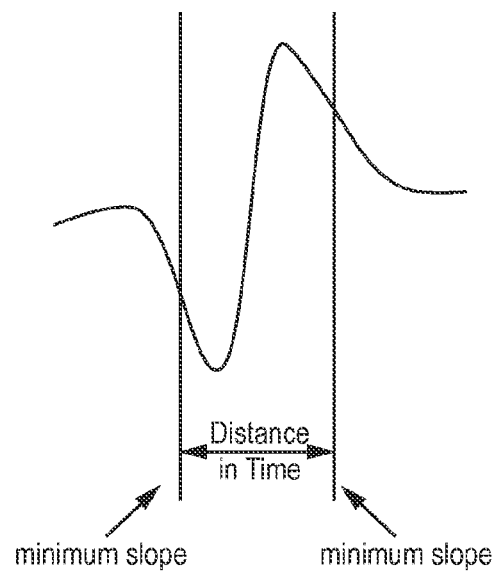
FIG. 34 graphically depicts an ambiguous signal acquired from a surface electrode associated with an electrode apparatus.

FIG. 34 depicts an ambiguous signal. The ambiguous signal includes two minimum slopes (i.e. steepest slopes) that are nearly equal and are separated by a distance (dis) of time that is less than the pre-selected number. If two separate slopes are about equal but are widely separated in time, then the signal acquired from a channel may be ambiguous from the standpoint of activation time detection. An ambiguous signal can still be a valid physiologic signal and may not be an artifact. But there is an element of ambiguity in determination of derivative-based activation time from such a signal. Decision block 1318 confirms whether a signal is ambiguous. For example, at block 1318, a determination is made as to whether the ratio is greater than a pre-selected number (e.g. where the pre-selected number can be any number from 1 to 5). The NO path from block 1318 continues to decision block 1320 which indicates the signal is ambiguous.

The YES path from block 1318 continues to block 1316 which indicates the signal is non-ambiguous (from the standpoint of derivative-based activation time determination). After determining whether a signal acquired from a channel is ambiguous or non-ambiguous, the process is finished at block 1322 for that particular channel. Method 1300 is repeated for each channel connected to an electrode until each signal channel has been processed.

The present disclosure can identify the timing of steepest negative slope of an unipolar ECG/cardiac signal for determining the activation time corresponding to a particular electrode. If the cardiac unipolar signal has a morphology with multiple negative slopes of comparable magnitudes, the present disclosure is able to identify the activation-time uniquely from that electrode, and reviews activation times from neighboring electrodes to determine the correct activation time.

FIGS. 15-19 and 21 are conceptual diagrams illustrating an example system 910 that is useful for obtaining an accurate onset and/or offset points of heart depolarization and repolarization waves of patient 914 according to the techniques described herein. As with the previously described system, in one example, system 910 may detect the onset and/or offset points of heart depolarization and repolarization waves in order to select a preferred location for implanting an intracardiac lead. In other examples, system 910 may detect the onset and/or offset points of heart depolarization and repolarization waves in order to select other parameters based on the electromechanical delay. For example, the system may select a particular pacing electrode configuration or pacing intervals for cardiac resynchronization therapy. In another example, with multipolar leads offering choices of more than one pacing electrode (cathode) in the ventricle, the system/device may automatically pace from each of the pacing electrodes at maximum pacing voltage and at a nominal atrio-ventricular delay (~100 ms) and measure onsets and offsets of the resulting depolarization waveforms on a far-field electrogram or on a leadless ECG or on a surface ECG lead, and choose the pacing electrode which produces the minimum difference between the offset of the local electrogram and the corresponding far-field onset, for delivery of cardiac resynchronization therapy. Alternatively, the pacing electrode which produces the narrowest far-field electrogram or surface ECG signal calculated as the difference between the offset and onset could be chosen. As illustrated in example diagram FIG. 15, a system 910 includes implantable medical device (IMD) 916, which is connected to leads 918, 920, and 922, and communicatively coupled to a programmer 924. IMD 916 senses electrical signals attendant to the depolarization and repolarization of heart 912, e.g., a cardiac EGM, via electrodes on one or more of leads 918, 920 and 922 or a housing of IMD 916. IMD 916 also delivers therapy in the form of electrical signals to heart 912 via electrodes located on one or more leads 918, 920, and 922 or a housing of IMD 916, such pacing, cardioversion and/or defibrillation pulses. IMD 916 may include or be coupled to various sensors, such as one or more accelerometers, for detecting other physiological parameters of patient 914, such as activity or posture.

In some examples, programmer 924 takes the form of a handheld computing device, computer workstation, or networked computing device that includes a user interface for presenting information to and receiving input from a user. A user, such as a physician, technician, surgeon, electrophysiologist, or other clinician, may interact with programmer 924 to communicate with IMD 916. For example, the user may interact with programmer 924 to retrieve physiological or diagnostic information from IMD 916. A user may also interact with programmer 924 to program IMD 916, e.g., select values for operational parameters of the IMD.

IMD 916 and programmer 924 may communicate via wireless communication using any techniques known in the art. Examples of communication techniques may include, for example, low frequency or radiofrequency (RF) telemetry, but other techniques are also contemplated. In some examples, programmer 924 may include a programming head that may be placed proximate to the patient's body near the IMD 916 implant site in order to improve the quality or security of communication between IMD 916 and programmer 924. In other examples, programmer 924 may be located remotely from IMD 916, and communicate with IMD 916 via a network.

The techniques for identifying onsets and/or offsets of cardiac electrogram waves may be performed by IMD 916, e.g., by a processor of IMD 916, based on one or more cardiac electrograms sensed by the IMD. In other examples, as described previously, some or all of the functions ascribed to IMD 916 or a processor thereof may be performed by one or more other devices, such as programmer 294 or a workstation (not shown), or a processor thereof. For example, programmer 924 may process EGM signals received from IMD 916 and/or cardiac mechanical contraction information to according to the techniques described herein. Furthermore, although described herein with respect to an IMD, in other examples, the techniques described herein may be performed by or implemented in an external medical device, which may be coupled to a patient via percutaneous or transcutaneous leads.

Figure 16:
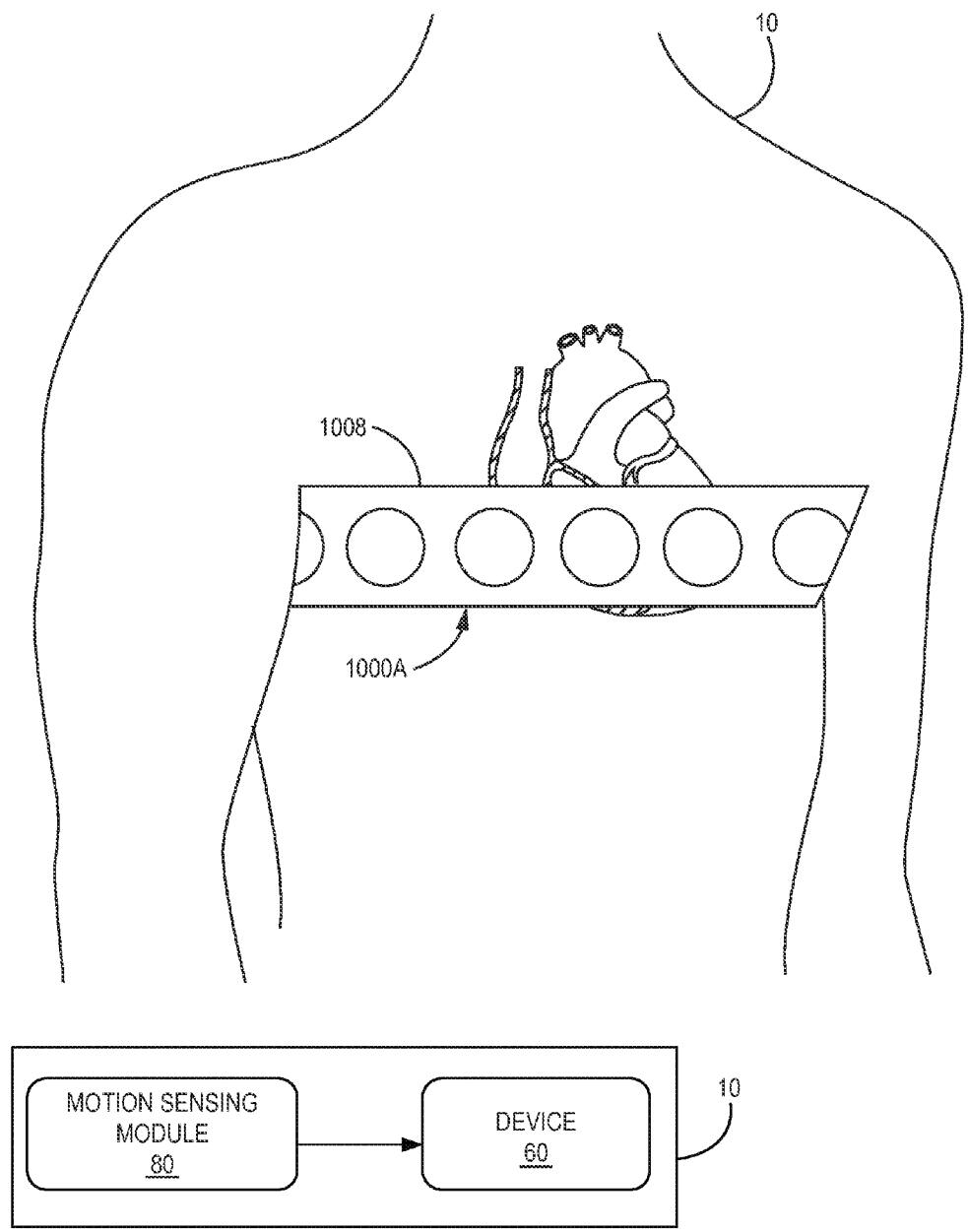
FIGS. 16-17 are conceptual diagrams illustrating exemplary systems for measuring torso-surface potentials.
Figure 17:
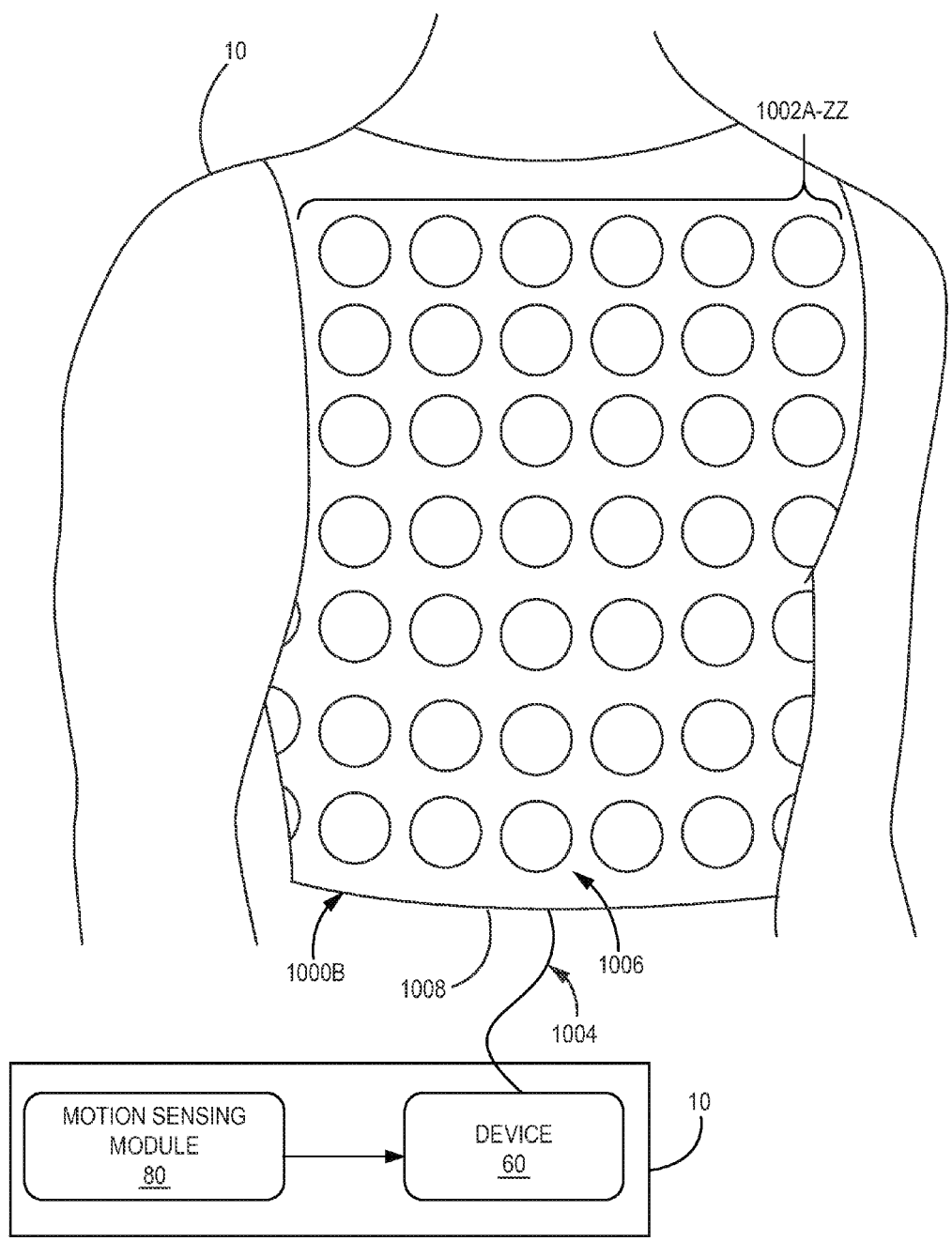

FIGS. 16 and 17 are conceptual diagrams illustrating example systems for measuring body-surface potentials and, more particularly, torso-surface potentials. In one example illustrated in FIG. 16, sensing device 1000A, comprising a set of electrodes 1002A-F (generically "electrodes 1002") and strap 1008, is wrapped around the torso of patient 914 such that the electrodes surround heart 912. As illustrated in FIG. 16, electrodes 1002 may be positioned around the circumference of patient 914, including the posterior, lateral, and anterior surfaces of the torso of patient 914. In other examples, electrodes 1002 may be positioned on any one or more of the posterior, lateral, and anterior surfaces of the torso. Electrodes 1002 may be electrically connected to a processing unit such as device 60 via wired connection 1004. Some configurations may use a wireless connection to transmit the signals sensed by electrodes 1002 to device 60, e.g., as channels of data.

Although in the example of FIG. 16 sensing device 1000A comprises strap 1008, in other examples any of a variety of mechanisms, e.g., tape or adhesives, may be employed to aid in the spacing and placement of electrodes 1002. In some examples, strap 1008 may comprise an elastic band, strip of tape, or cloth. In some examples, electrodes 1002 may be placed individually on the torso of patient 914.

Electrodes 1002 may surround heart 912 of patient 914 and record the electrical signals associated with the depolarization and repolarization of heart 912 after the signals have propagated through the torso of patient 914. Each of electrodes 1002 may be used in a unipolar configuration to sense the torso-surface potentials that reflect the cardiac signals. Device 60 may also be coupled to a return or indifferent electrode (not shown) which may be used in combination with each of electrodes 1002 for unipolar sensing. In some examples, there may be 12 to 16 electrodes 1002 spatially distributed around the torso of patient 914. Other configurations may have more or fewer electrodes 1002.

Processing unit 60 may record and analyze the torso-surface potential signals sensed by electrodes 1002. As described herein, device 60 may be configured to provide an output to a user. The user may make a diagnosis, prescribe CRT, position therapy devices, e.g., leads, or adjust or select treatment parameters based on the indicated output.

In some examples, the analysis of the torso-surface potential signals by device 60 may take into consideration the location of electrodes 1002 on the surface of the torso of patient 914. In such examples, device 60 may be communicatively coupled to a motion sensing module 80 such as a programmer, which may provide an image that allows device 60 to determine coordinate locations of each of electrodes 1002 on the surface of patient 914. Electrodes 1002 may be visible, or made transparent through the inclusion or removal of certain materials or elements, in the image provided by motion sensing module 80.

FIG. 17 illustrates an example configuration of a system that may be used to evaluate cardiac response in heart 912 of patient 914. The system comprises a sensing device 1000B, which may comprise vest 1006 and electrodes 1002 A-ZZ (generically "electrodes 1002"), a device 60, and imaging system 501. Device 60 and imaging system 501 may perform substantially as described above with respect to FIG. 15. As illustrated in FIG. 17, electrodes 1002 are distributed over the torso of patient 914, including the anterior, lateral, and posterior surfaces of the torso of patient 914.

Sensing device 1000B may comprise a fabric vest 1006 with electrodes 1002 attached to the fabric. Sensing device 10008 may maintain the position and spacing of electrodes 1002 on the torso of patient 914. Sensing device 10008 may be marked to assist in determining the location of electrodes 1002 on the surface of the torso of patient 914. In some examples, there may be 150 to 256 electrodes 1002 distributed around the torso of patient 914 using sensing device 10008, though other configurations may have more or fewer electrodes 1002.

The ECG data is mapped to a generic, graphical model of a patient's torso and/or heart and a graphical display is produced on a graphical user interface without taking an actual image, such as an MRI or CT image, from the patient. The resolution of the ECG data mapped to a graphical anatomical model depends on the number and spacing of surface electrodes 1002 used. In some examples, there may be 12 to 16 electrodes spatially distributed around the torso of patient 914. Each electrode is associated with a channel that is connected in a processor. Other configurations may have more or fewer electrodes. In one embodiment, a minimum number of electrodes includes twelve electrodes arranged in two rows extending along the posterior torso and twelve electrodes arranged in two rows extending along the anterior torso for a total of twenty-four electrodes, which may be equally distributed circumferentially around the torso. The number of electrodes can be greater than 12 electrodes. In one or more examples presented in methods 100-300, 56 channels associated with 56 electrodes are used but skilled artisans will understand that more or less electrodes can be used to with these methods. Another exemplary system with a computing apparatus or processor, electrode apparatus and display apparatus that can be used is described in U.S. patent application Ser. No. 14/227,955 filed on Mar. 27, 2014 entitled SYSTEMS, METHODS, AND INTERFACES FOR IDENTIFYING EFFECTIVE ELECTRODES, by Ghosh et al. and incorporated by reference in its entirety. Reliable detection of depolarization waves assists the physician in setting parameters for optimal delivery of CRT.

Figure 18:
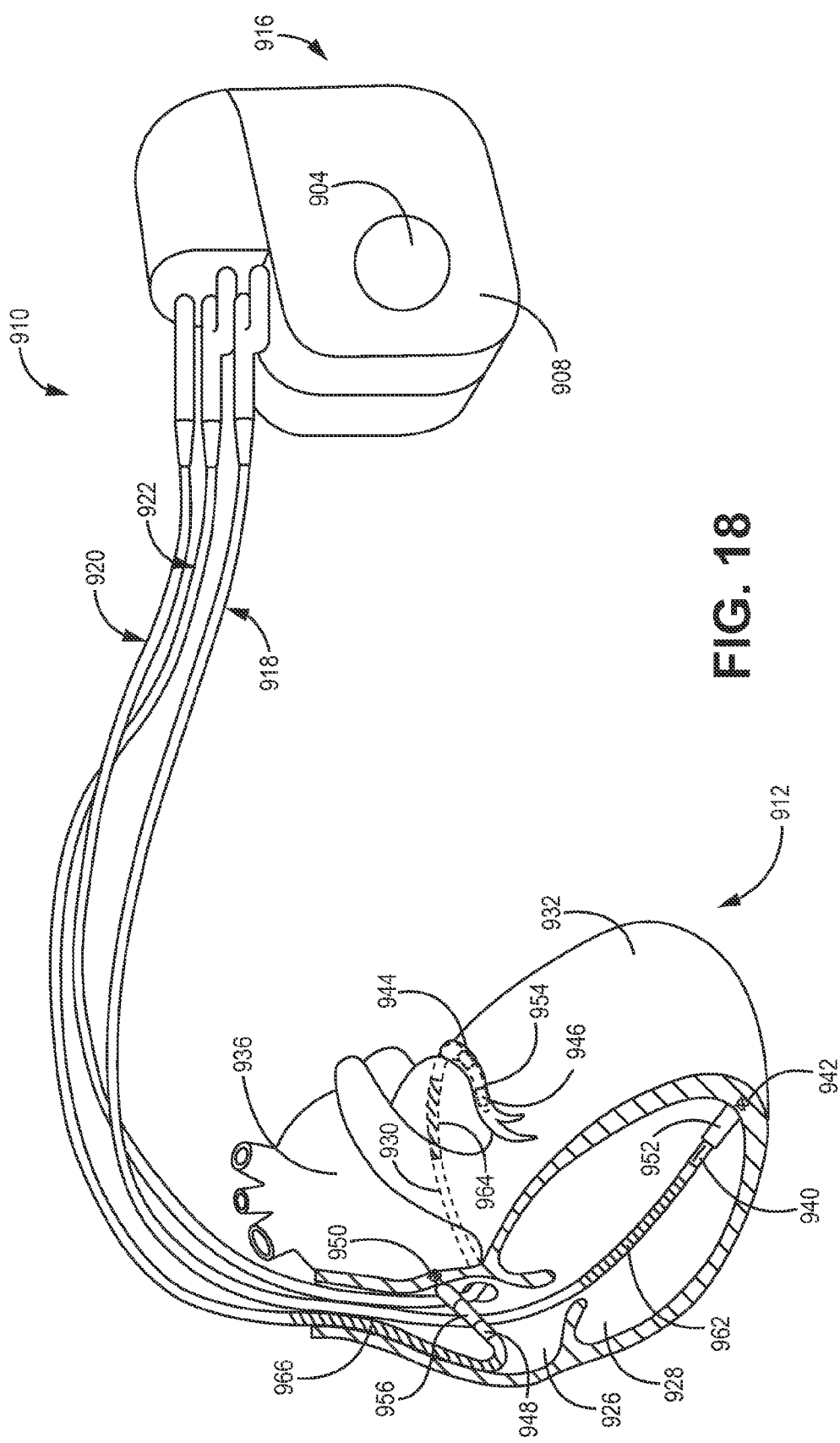
FIG. 18 is a conceptual diagram illustrating the implantable medical device (IMD) and leads of the system shown in FIG. 15 in greater detail.

FIG. 18 is a conceptual diagram illustrating IMD 916 and leads 918, 920, and 922 of system 910 in greater detail. In the illustrated example, bipolar electrodes 940 and 942 are located adjacent to a distal end of lead 918. In addition, bipolar electrodes 944 and 946 are located adjacent to a distal end of lead 920, and bipolar electrodes 948 and 950 are located adjacent to a distal end of lead 922.

In the illustrated example, electrodes 940, 944 and 948 take the form of ring electrodes, and electrodes 942, 946 and 950 may take the form of extendable helix tip electrodes mounted retractably within insulative electrode heads 952, 954 and 956, respectively. Leads 918, 920, 922 also include elongated electrodes 962, 964, 966, respectively, which may take the form of a coil. In some examples, each of the electrodes 940, 942, 944, 946, 948, 950, 962, 964 and 966 is electrically coupled to a respective conductor within the lead body of its associated lead 918, 920, 922, and thereby coupled circuitry within IMD 916.

In some examples, IMD 916 includes one or more housing electrodes, such as housing electrode 904 illustrated in FIG. 18, which may be formed integrally with an outer surface of hermetically-sealed housing 908 of IMD 916 or otherwise coupled to housing 908. In some examples, housing electrode 904 is defined by an uninsulated portion of an outward facing portion of housing 908 of IMD 916. Other division between insulated and uninsulated portions of housing 908 may be employed to define two or more housing electrodes. In some examples, a housing electrode comprises substantially all of housing 908.

As described in further detail with reference to FIG. 19, housing 908 encloses a signal generator that generates therapeutic stimulation, such as cardiac pacing, cardioversion and defibrillation pulses, as well as a sensing module for sensing electrical signals attendant to the depolarization and repolarization of heart 912. Housing 908 may also enclose a wave detection module that detects the onsets and/or offsets of heart depolarization and repolarization waves. The wave detection module may be enclosed within housing 908. Alternatively, the wave detection module may be housed in a remote piece of equipment, such as programmer 924 or a workstation (not shown) and communicate with the IMD 916 through wireless communication.

IMD 916 senses electrical signals attendant to the depolarization and repolarization of heart 912 via electrodes 904, 940, 942, 944, 946, 948, 950, 962, 964 and 966. IMD 916 may sense such electrical signals via any bipolar combination of electrodes 940, 942, 944, 946, 948, 950, 962, 964 and 966. Furthermore, any of the electrodes 940, 942, 944, 946, 948, 950, 962, 964 and 966 may be used for unipolar sensing in combination with housing electrode 904.

In some examples, IMD 916 delivers pacing pulses via bipolar combinations of electrodes 940, 942, 944, 946, 948 and 950 to produce depolarization of cardiac tissue of heart 912. In some examples, IMD 16 delivers pacing pulses via any of electrodes 940, 942, 944, 946, 948 and 950 in combination with housing electrode 904 in a unipolar configuration. Furthermore, IMD 916 may deliver cardioversion or defibrillation pulses to heart 12 via any combination of elongated electrodes 962, 964, 966, and housing electrode 904.

The illustrated numbers and configurations of leads 918, 920, and 922 and electrodes are merely examples. Other configurations, i.e., number and position of leads and electrodes, are possible. In some examples, system 910 may include an additional lead or lead segment having one or more electrodes positioned at different locations in the cardiovascular system for sensing and/or delivering therapy to patient 914. For example, instead of or in addition to intracardiac leads 918, 920 and 922, system 910 may include one or more epicardial or subcutaneous leads not positioned within the heart. In some examples, the subcutaneous leads may sense a subcutaneous cardiac electrogram, for example the far-field electrogram between the SVC coil and the can. The subcutaneous cardiac electrogram may substitute for the surface ECG in determining the global electromechanical delay.

Figure 19:
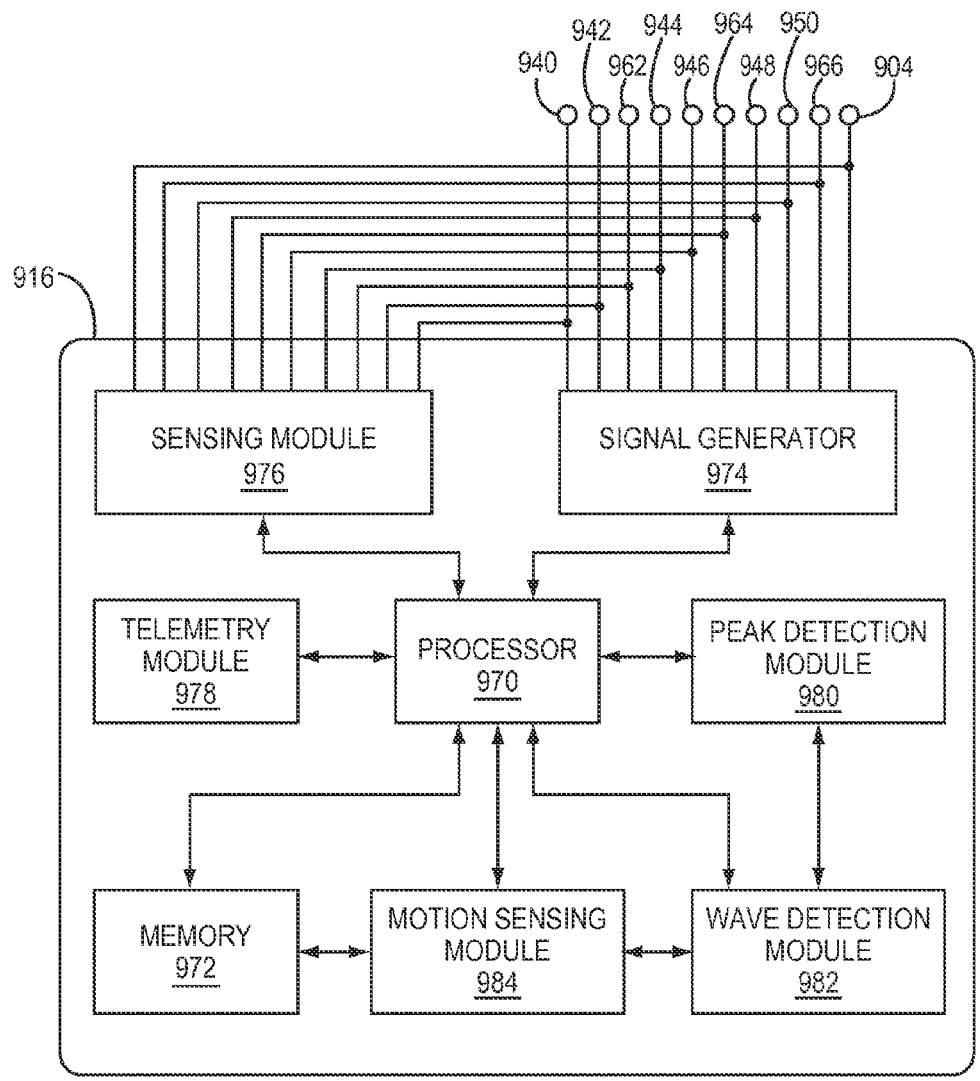
FIG. 19 is a block diagram of an example implantable medical device that may determine the onset and offset of heart depolarization and repolarization waves.

FIG. 19 is a block diagram illustrating an example configuration of IMD 916. In the illustrated example, IMD 916 includes a processor 970, memory 972, signal generator 974, sensing module 976, telemetry module 978, motion sensing module 980, wave detection module 982 and peak detection module 984. Memory 972 includes computer-readable instructions that, when executed by processor 970, causes IMD 916 and processor 970 to perform various functions attributed to IMD 916 and processor 970 herein. Memory 972 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 970 may include any one or more of a microprocessor, a controller, a digital signal processor (DSP), an application specific integrated circuit (ASIC), a field-programmable gate array (FPGA), or equivalent discrete or analog logic circuitry. In some examples, processor 970 may include multiple components, such as any combination of one or more microprocessors, one or more controllers, one or more DSPs, one or more ASICs, or one or more FPGAs, as well as other discrete or integrated logic circuitry. The functions attributed to processor 970 herein may be embodied as software, firmware, hardware or any combination thereof. Generally, processor 970 controls signal generator 974 to deliver stimulation therapy to heart 912 of patient 914 according to a selected one or more of therapy programs or parameters, which may be stored in memory 972. As an example, processor 970 may control signal generator 974 to deliver electrical pulses with the amplitudes, pulse widths, frequency, or electrode polarities specified by the selected one or more therapy programs.

Signal generator 974 is configured to generate and deliver electrical stimulation therapy to patient 912. As shown in FIG. 19, signal generator 974 is electrically coupled to electrodes 94, 940, 942, 944, 946, 948, 950, 962, 964, and 966, e.g., via conductors of the respective leads 918, 920, and 922 and, in the case of housing electrode 904, within housing 908. For example, signal generator 974 may deliver pacing, defibrillation or cardioversion pulses to heart 912 via at least two of electrodes 94, 940, 942, 944, 946, 948, 950, 962, 964, and 966. In other examples, signal generator 974 delivers stimulation in the form of signals other than pulses, such as sine waves, square waves, or other substantially continuous time signals.

Signal generator 974 may include a switch module (not shown) and processor 970 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes. Electrical sensing module 976 monitors electrical cardiac signals from any combination of electrodes 904, 940, 942, 944, 946, 948, 950, 962, 964, and 966. Sensing module 976 may also include a switch module which processor 970 controls to select which of the available electrodes are used to sense the heart activity, depending upon which electrode combination is used in the current sensing configuration.

Sensing module 976 may include one or more detection channels, each of which may comprise an amplifier. The detection channels may be used to sense the cardiac signals. Some detection channels may detect events, such as R-waves or P-waves, and provide indications, such as wave markers, of the occurrences of such events to processor 970. One or more other detection channels may provide the signals to an analog-to-digital converter, for conversion into a digital signal for processing or analysis by processor 970.

For example, sensing module 976 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 970 then uses that detection in measuring frequencies of the sensed events.

In one example, at least one narrow band channel may include an R-wave or P-wave amplifier. In some examples, the R-wave and P-wave amplifiers may take the form of an automatic gain controlled amplifier that provides an adjustable sensing threshold as a function of the measured R-wave or P-wave amplitude. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

In some examples, sensing module 976 includes a wide band channel which may comprise an amplifier with a relatively wider pass band than the narrow band channels. Signals from the electrodes that are selected for coupling to this wide-band amplifier may be converted to multi-bit digital signals by an analog-to-digital converter (ADC) provided by, for example, sensing module 976 or processor 970. Processor 970 may analyze the digitized versions of signals from the wide band channel. Processor 970 may employ digital signal analysis techniques to characterize the digitized signals from the wide band channel to, for example, detect and classify the patient's heart rhythm.

Processor 970 may detect and classify the patient's heart rhythm based on the cardiac electrical signals sensed by sensing module 976 employing any of the numerous signal processing methodologies known in the art. For example, processor 970 may maintain escape interval counters that may be reset upon sensing of R-waves by sensing module 976. The value of the count present in the escape interval counters when reset by sensed depolarizations may be used by processor 970 to measure the durations of R-R intervals, which are measurements that may be stored in memory 972. Processor 970 may use the count in the interval counters to detect a tachyarrhythmia, such as ventricular fibrillation or ventricular tachycardia. A portion of memory 972 may be configured as a plurality of recirculating buffers, capable of holding series of measured intervals, which may be analyzed by processor 970 to determine whether the patient's heart 912 is presently exhibiting atrial or ventricular tachyarrhythmia.

In some examples, processor 970 may determine that tachyarrhythmia has occurred by identification of shortened R-R interval lengths. Generally, processor 970 detects tachycardia when the interval length falls below 360 milliseconds (ms) and fibrillation when the interval length falls below 320 ms. These interval lengths are merely examples, and a user may define the interval lengths as desired, which may then be stored within memory 972. This interval length may need to be detected for a certain number of consecutive cycles, for a certain percentage of cycles within a running window, or a running average for a certain number of cardiac cycles, as examples.

In some examples, an arrhythmia detection method may include any suitable tachyarrhythmia detection algorithms. In one example, processor 970 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 970 in other examples. For example, EGM morphology may be considered in addition to or instead of interval length for detecting tachyarrhythmias.

Generally, processor 970 detects a treatable tachyarrhythmia, such as VF, based on the EGM, e.g., the R-R intervals and/or morphology of the EGM, and selects a therapy to deliver to terminate the tachyarrhythmia, such as a defibrillation pulse of a specified magnitude. The detection of the tachyarrhythmia may include a number of phases or steps prior to delivery of the therapy, such as first phase, sometimes referred to as detection, in which a number of consecutive or proximate R-R intervals satisfies a first number of intervals to detect (NID) criterion, a second phase, sometimes referred to as confirmation, in which a number of consecutive or proximate R-R intervals satisfies a second, more restrictive NID criterion. Tachyarrhythmia detection may also include confirmation based on EGM morphology or other sensors subsequent to or during the second phase.

In the illustrated example, IMD 916 also includes peak detection module 980, wave detection module 982, and motion sensing module 984. Peak detection module 980 and wave detection module 982 may be configured and provide the functionality ascribed to peak detection module 76 and wave detection module 78 herein. Peak detection module 980 may be configured to determine a maximum value of a particular signal. For example, peak detection module 980 may be configured to receive an electrical signal from wave detection module 982 or processor 970 and determine a maximum value of the received signal. Peak detection module 980 may, in some examples, comprise a narrowband channel of sensing module 976 that is configured to detect R-waves, P-waves, or T-waves in cardiac electrogram signals, e.g., using an amplifier with automatically adjusting threshold.

Generally, wave detection module 982 determines the onsets and/or offsets on the heart depolarization and repolarizations waves. Wave detection module 982 may be similar to the wave detection module described previously, e.g. wave detection module 78, and more accurately described in FIG. 2. For example, wave detection module may include a low-pass filter, a window module, a slope module, a rectifier module, a smoothing module, and a threshold detection module. Wave detection module 982 may perform substantially similar to the wave detection module described previously in this application.

Peak detection module 980 and wave detection module 982 may receive a cardiac electrogram from sensing module 976, e.g., from a wide-band channel of the sensing module. In some examples, the cardiac electrogram may be a far-field cardiac electrogram, e.g., between superior vena cava coil 766 and housing electrode 904. A far-field cardiac electrogram may be used in the manner described herein with respect to a surface ECG, e.g., to determine a global electromechanical delay. In some examples, the cardiac electrogram may be a unipolar cardiac electrogram between housing electrode 906 and any of electrodes 942, 944, 946 and 950. The unipolar cardiac electrogram may be received from sensing module 976, e.g., via a wide-band channel of the sensing module, and may be used in the manner described herein with respect to local cardiac electrogram signals, e.g., to determine local electromechanical delays.

Motion sensing module 984 may sense the mechanical contraction of the heart, e.g., at one or more cardiac sites. Motion sensing module 984 may be electrically coupled to one or more sensors that generate a signal that varies based on cardiac contraction or motion generally, such as one or more accelerometers, pressure sensors, impedance sensors, or flow sensors. The detected contraction may be contraction of cardiac tissue at a particular location, e.g., a particular portion of a ventricular wall.

Although processor 970 and wave detection module 982 are illustrated as separate modules in FIG. 19, processor 970 and wave detection module 982 may be incorporated in a single processing unit. Wave detection module 982, and any of its components, may be a component of or module executed by processor 970.

Figure 15:
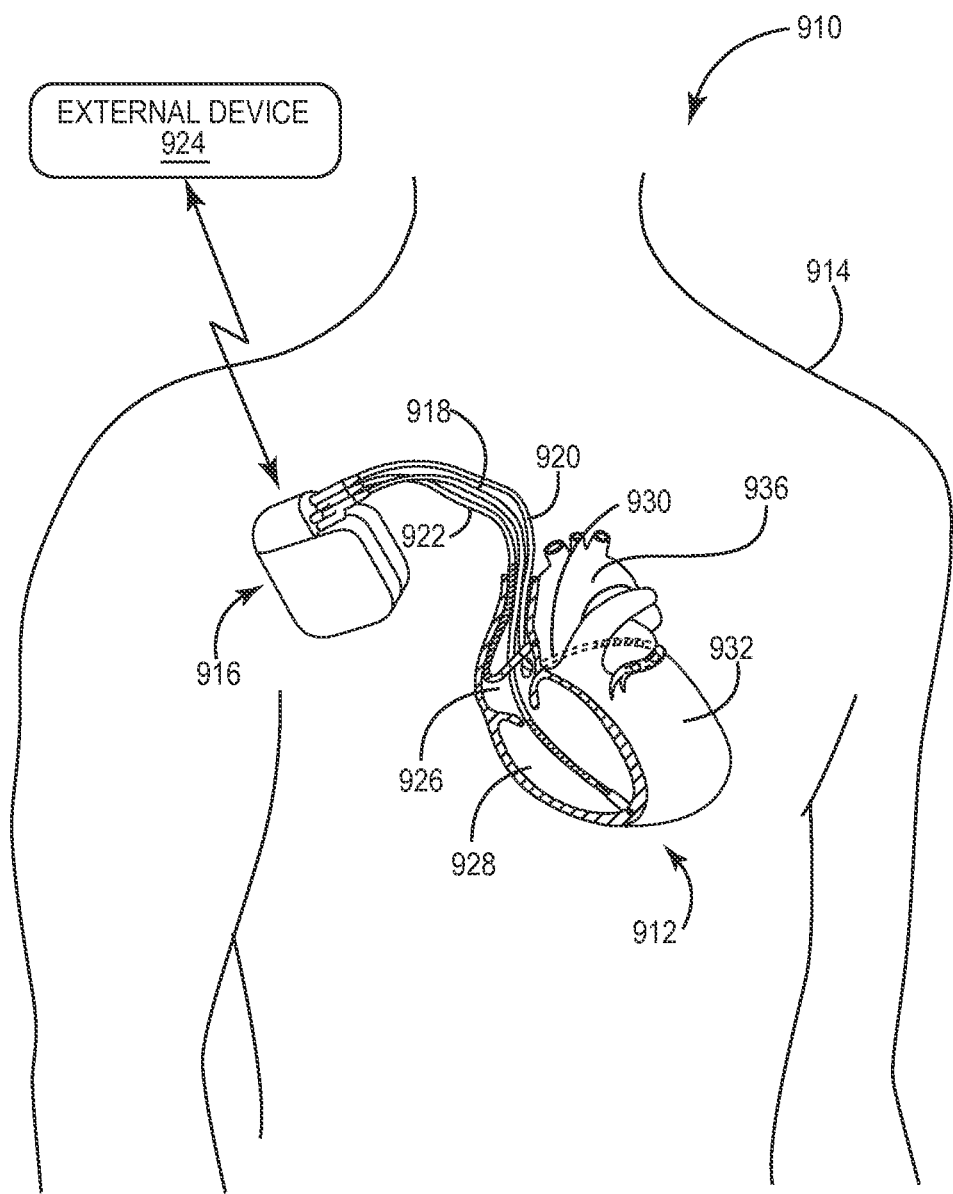
FIG. 15 is a conceptual diagram illustrating an example system that determines the onset and offsets of heart depolarization and repolarization waves.

Telemetry module 978 includes any suitable hardware, firmware, software or any combination thereof for communicating with another device, such as programmer 924 (FIG. 15). In some examples, programmer 924 may include a programming head that is placed proximate to the patient's body near the IMD 916 implant site, and in other examples programmer 924 and IMD 916 may be configured to communicate using a distance telemetry algorithm and circuitry that does not require the use of a programming head and does not require user intervention to maintain a communication link. Under the control of processor 970, telemetry module 978 may receive downlink telemetry from and send uplink telemetry to programmer 924 with the aid of an antenna, which may be internal and/or external. In some examples, processor 970 may transmit cardiac signals produced by sensing module 976 and/or signals generated by heart sound sensor 982 to programmer 924. Processor 970 may also generate and store marker codes indicative of different cardiac events that sensing module 976 or heart sound analyzer 980 detects, and transmit the marker codes to programmer 924. An example IMD with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety. Information which processor 970 may transmit to programmer 924 via telemetry module 978 may also include indications of treatable rhythms, and indications of non-treatable rhythms in which the EGM based indication indicated that the rhythm was treatable and the heart sound based indication indicated that the rhythm was non-treatable. Such information may be included as part of a marker channel with an EGM.

Implementation of the methods disclosed herein requires a plurality of body-surface electrodes such as an ECG belt or vest be placed around the torso of the patient. An exemplary ECG belt or vest is described in U.S. patent application Ser. No. 13/462,404, filed May 2, 2012, entitled "Assessing Intra-Cardiac Activation Patterns And Electrical Dyssynchrony" and assigned to the assignee of the present invention, the disclosure of which is incorporated by reference in its entirety herein. After the vest or belt is secured around the patient's torso, the programmer is activated. Exemplary programmers that can be used to acquire signals from implanted and surface electrodes includes the Medtronic Carelink Programmer Model 2090 and the Model 2290 Analyzer or the CARELINK ENCORE™. Medtronic Vitatron Reference Manual CARELINK ENCORE™ (2013) available from Medtronic.

Figure 21:
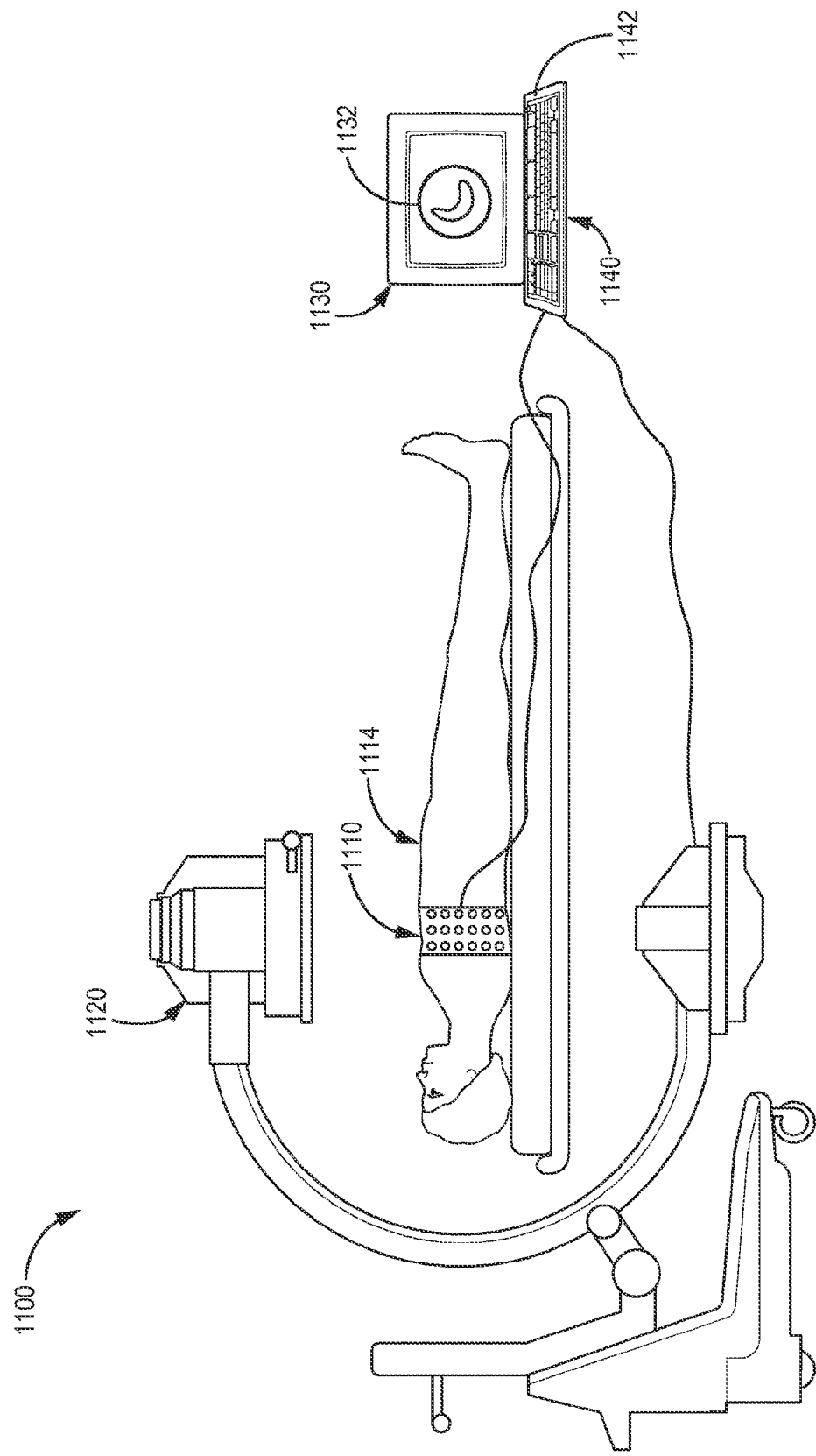
FIG. 21 is a diagram of an exemplary system including electrode apparatus, imaging apparatus, display apparatus, and computing apparatus.
Figure 22:
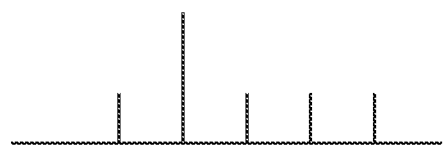
FIG. 22 is a schematic diagram depicting a maximum and several closely spaced apart local maximums associated with a potentially valid signal as processed through block 324 of FIG. 7.

An exemplary system 1100 can be used to acquire data to determine the most onset of cardiac depolarization and or offset of repolarization waves. System 1100 including electrode apparatus 1110, imaging apparatus 1120, display apparatus 1130, and computing apparatus 1140 is depicted in FIG. 21. The electrode apparatus 1110 as shown includes a plurality of electrodes incorporated, or included within a band wrapped around the chest, or torso, of a patient. The electrode apparatus 1110 is operatively coupled to the computing apparatus 1140 (e.g., through one or more wired electrical connections, wirelessly, etc.) to provide electrical signals from each of the electrodes to the computing apparatus 1140 for analysis. Exemplary electrode apparatus may be described in U.S. Provisional Patent Application 61/913, 759 entitled "Bioelectric Sensor Device and Methods" and filed on Dec. 9, 2013 and U.S. Patent Application entitled "Bioelectric Sensor Device and Methods" and filed on even date herewith, each of which is incorporated herein by reference in its entirety.

The imaging apparatus 1120 may be any type of imaging apparatus configured to image, or provide images of, at least a portion of the patient in a non-invasive manner. For example, the imaging apparatus 1120 may not use any components or parts that may be located within the patient to provide images of at least a portion of the patient except non-invasive tools such as contrast solution. It is to be understood that the exemplary systems, methods, and interfaces described herein may noninvasively assist a user (e.g., a physician) in selecting a location proximate a patient's heart for an implantable electrode, and after the exemplary systems, methods, and interfaces have provided noninvasive assistance, the exemplary systems, methods, and interfaces may then provide assistance to implant, or navigate, an implantable electrode into the patient, e.g., proximate the patient's heart.

For example, after the exemplary systems, methods, and interfaces have provided noninvasive assistance, the exemplary systems, methods, and interfaces may then provide image guided navigation that may be used to navigate leads including electrodes, leadless electrodes, wireless electrodes, catheters, etc., within the patient's body. Further, although the exemplary systems, methods, and interfaces are described herein with reference to a patient's heart, it is to be understood that the exemplary systems, methods, and interfaces may be applicable to any other portion of the patient's body.

The imaging apparatus 1120 may be configured to capture, or take, x-ray images (e.g., two dimensional x-ray images, three dimensional x-ray images, etc.) of the patient. The imaging apparatus 1120 may be operatively coupled (e.g., through one or more wired electrical connections, wirelessly, etc.) to the computing apparatus 140 such that the images captured by the imaging apparatus) 120 may be transmitted to the computing apparatus 1140. Further, the computing apparatus 1140 may be configured to control the imaging apparatus 1120 to, e.g., configure the imaging apparatus 1120 to capture images, change one or more settings of the imaging apparatus 1120, etc.

It will be recognized that while the imaging apparatus 1120 as shown in FIG. 21 may be configured to capture x-ray images, any other alternative imaging modality may also be used by the exemplary systems, methods, and interfaces described herein. For example, the imaging apparatus 1120 may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative MRI, etc. Further, it is to be understood that the imaging apparatus 120 may be configured to capture a plurality of consecutive images (e.g., continuously) to provide video frame data. In other words, a plurality of images taken over time using the imaging apparatus 120 may provide motion picture data. Additionally, the images may also be obtained and displayed in two, three, or four dimensions. In more advanced forms, four-dimensional surface rendering of the heart or other regions of the body may also be achieved by incorporating heart data or other soft tissue data from an atlas map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data to be used to confidently reach target locations within the heart or other areas of interest.

The display apparatus 1130 and the computing apparatus 140 may be configured to display and analyze data such as, e.g., surrogate electrical activation data, image data, mechanical motion data, etc. gathered, or collected, using the electrode apparatus 1110 and the imaging apparatus 1120 to noninvasively assist a user in location selection of an implantable electrode. In at least one embodiment, the computing apparatus 140 may be a server, a personal computer, or a tablet computer. The computing apparatus 140 may be configured to receive input from input apparatus 1142 and transmit output to the display apparatus 1130. Further, the computing apparatus 1140 may include data storage that may allow for access to processing programs or routines and/or one or more other types of data, e.g., for driving a graphical user interface configured to noninvasively assist a user in location selection of an implantable electrode, etc.

The computing apparatus 1140 may be operatively coupled to the input apparatus 1142 and the display apparatus 1130 to, e.g., transmit data to and from each of the input apparatus 1142 and the display apparatus 1130. For example, the computing apparatus 1140 may be electrically coupled to each of the input apparatus 1142 and the display apparatus 1130 using, e.g., analog electrical connections, digital electrical connections, wireless connections, bus-based connections, network-based connections, internet-based connections, etc. As described further herein, a user may provide input to the input apparatus 1142 to manipulate, or modify, one or more graphical depictions displayed on the display apparatus 1130 to view and/or select one or more target or candidate locations of a portion of a patient's heart as further described herein.

Although as depicted the input apparatus 1142 is a keyboard, it is to be understood that the input apparatus 1142 may include any apparatus capable of providing input to the computing apparatus 1140 to perform the functionality, methods, and/or logic described herein. For example, the input apparatus 1142 may include a mouse, a trackball, a touchscreen (e.g., capacitive touchscreen, a resistive touchscreen, a multi-touch touchscreen, etc.), etc. Likewise, the display apparatus 1130 may include any apparatus capable of displaying information to a user, such as a graphical user interface 132 including graphical depictions of anatomy of a patient's heart, images of a patient's heart, graphical depictions of locations of one or more electrodes, graphical depictions of one or more target or candidate locations, alphanumeric representations of one or more values, graphical depictions or actual images of implanted electrodes and/or leads, etc. For example, the display apparatus 1130 may include a liquid crystal display, an organic light-emitting diode screen, a touchscreen, a cathode ray tube display, etc.

The graphical user interfaces 1132 displayed by the display apparatus 130 may include, or display, one or more regions used to display graphical depictions, to display images, to allow selection of one or more regions or areas of such graphical depictions and images, etc. As used herein, a "region" of a graphical user interface 1132 may be defined as a portion of the graphical user interface 1132 within which information may be displayed or functionality may be performed. Regions may exist within other regions, which may be displayed separately or simultaneously. For example, smaller regions may be located within larger regions, regions may be located side-by-side, etc. Additionally, as used herein, an "area" of a graphical user interface 1132 may be defined as a portion of the graphical user interface 1132 located with a region that is smaller than the region it is located within. Exemplary systems and interfaces may be described in U.S. Provisional Patent Application 61/913,743 entitled "Noninvasive Cardiac Therapy Evaluation" and filed on Dec. 9, 2013 and U.S. Patent Application entitled "Noninvasive Cardiac Therapy Evaluation" and filed on even date herewith, each of which is incorporated herein by reference in its entirety.

The processing programs or routines stored and/or executed by the computing apparatus 1140 may include programs or routines for computational mathematics, matrix mathematics, decomposition algorithms, compression algorithms (e.g., data compression algorithms), calibration algorithms, image construction algorithms, signal processing algorithms (e.g., Fourier transforms, fast Fourier transforms, etc.), standardization algorithms, comparison algorithms, vector mathematics, or any other processing required to implement one or more exemplary methods and/or processes described herein. Data stored and/or used by the computing apparatus 1140 may include, for example, image data from the imaging apparatus 1120, electrical signal data from the electrode apparatus 1110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein, or any other data that may be necessary for carrying out the one and/or more processes or methods described herein.

Far-field EGMs, ECG, or ECG-like signals are acquired from an electrode that is the greatest distance away from the pacing electrode. If an IMD is implanted, electrodes that can produce far field signals include superior vena cava (SVC) electrode-pulse generator housing (also referred to as a "can"), right ventricle (RV) coil-can etc.).

Additionally, pre-specified windows can be defined as extending from the atrial marker to the ventricular marker.

A low pass filter is then applied to the ECG signal within the pre-specified window. The low-pass filter can be a Bessel filter with a cut-off frequency of 15 Hz, 20 Hz or a frequency value between 15 Hz and 20 Hz. The signal(s) acquired from the plurality of surface electrodes and/or the electrodes associated with the implantable medical device is passed through the low pass filter, which causes the removal of any spurious high-frequency artifacts or components from the far-field ECG-like signal.

A rectified slope of the signal within the window is determined at block 1108 using module 96 depicted in FIG. 2. Rectification of a signal can be performed by any known method.

The techniques described in this disclosure, including those attributed to IMD wave detection module 80, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Additionally, skilled artisans understand that the system and/or method automatically store any result from a calculation or determination.

There are a variety of other embodiments that can be employed for the pre-specified window used in FIG. 15. For example, the pre-specified window can be set to begin at an atrial wave marker and extend a certain length of time or to another marker. In yet another embodiment, the pre-specified window can be set to begin at a ventricular wave marker and extend a certain length of time or to another marker.

Exemplary systems that can be employ one or more methods described herein include U.S. Pat. No. 8,887,736, U.S. Pat. No. 8,532,734B2, U.S. Pat. No. 8,457,371 B2, U.S. Pat. No. 8,442,625B2, U.S. Pat. No. 8,424,536B2, U.S. Pat. No. 8,421,799B2, U.S. Pat. No. 8,391,965B2, U.S. Pat. No. 8,364,252B2, U.S. Pat. No. 8,345,067B2, US20120130232A1, U.S. Pat. No. 8,185,192B2, U.S. Pat. No. 8,106,905B2, US20090265128A1, US20090264751A1, US20090264750A1, US20090264749A1, US20090264748A1, US20090264747A1, US20090264746A1, US20090264727A1, US20090262992A1, US20090262109A1, U.S. Pat. No. 8,843,189B2, U.S. Pat. No. 8,839,798B2, U.S. Pat. No. 8,839,798B2, U.S. Pat. No. 8,663,120B2, U.S. Pat. No. 8,660,640B2, U.S. Pat. No. 8,560,042B2, U.S. Pat. No. 8,494,608B2, U.S. Pat. No. 8,340,751 B2, U.S. Pat. No. 8,260,395B2, US20120190993A1, U.S. Pat. No. 8,214,018B2, U.S. Pat. No. 8,208,991 B2, US20090297001 A1, US20090264777A1, US20090264752A1, US20090264743A1, US20090264742A1, U.S. Pat. No. 8,831,701B2, U.S. Pat. No. 8,494,614B2, US20100004724A1, U.S. Pat. No. 6,263,235 B1 all of which are incorporated by reference in their entirety.

Exemplary embodiments are as follows:

Embodiment 1 is a system for use in monitoring cardiac signals comprising:
    an electrode apparatus comprising a plurality of electrodes configured to be located proximate tissue of a patient;
    display apparatus comprising a graphical user interface, wherein the graphical user interface is configured to present information to a user;
    computing apparatus coupled to the electrode apparatus and display apparatus, wherein the computing apparatus is configured to determine whether a signal acquired from a channel associated with an electrode from the plurality of electrodes is valid and sufficiently strong by:

i) calculating a first derivative of the signal;
ii) determining a minimum and maximum of the first derivative;
iii) determining whether signs of the minimum and maximum of the first derivative are different; and
in response to determining whether the signs of the minimum and maximum of the first derivative are different, displaying on the graphical user interface whether the signal is valid.

Embodiment 2 is the system of embodiment 1, wherein the signal is declared valid when the signs of the minimum and maximum of the first derivative are the same.

Embodiment 3 is the system of embodiments 2-3 further comprising:
calculating a ratio of an absolute value of a larger first derivative value to an absolute value of a smaller first derivative value.

1. Embodiment 4 is the system of embodiment 4 further comprising: determining whether the ratio is greater than a pre-selected number; and in response to determining whether the ratio is greater than a pre-selected number, determining whether the signal is valid.

2. Embodiment 5 is the system of any of embodiments 1-4 wherein in response to determining the signs of the minimum and maximum of the first derivative are different, declaring the signal is valid.

3. Embodiment 6 is the system of any of embodiments 1-5 wherein in response to determining the signs of the minimum and maximum of the first derivative are the same, declaring the signal is invalid.

4. Embodiment 7 is a method for determining whether a signal is valid or an artifact in a multichannel mapping system, the multichannel mapping system comprising a processor connected to an electrode apparatus and a display apparatus, the electrode apparatus located proximate tissue of a patient, wherein the processor is configured to determine whether a signal acquired from a channel associated with an electrode from the plurality of electrodes is valid, the method comprising:
acquiring a signal from an electrode associated with an electrode apparatus allows the processor, executing a set of instructions, to perform a set of actions comprising:
i) calculating a first derivative of the signal;
ii) determining a minimum and maximum from the first derivative;
iii) determining whether signs of the minimum and maximum are different; and
in response to determining whether signs of the minimum and maximum are different, displaying on the display apparatus whether the signal is valid.

Embodiment 8 is the embodiment of claim 7, wherein the signal is declared valid in response to determining the signs of the minimum and maximum are the same.

Embodiment 9 is the method of embodiment 7, wherein the signal is declared invalid in response to determining the signs of the minimum and maximum are different.

Embodiment 10 is the method of embodiment 7 wherein the invalid signal is determined to be an artifact.

Embodiment 11 is the method of embodiments 1-10, further comprising:
eliminating any channel or electrode for use in a multichannel system in which an invalid signal is acquired.

Embodiment 12 is the method of embodiment 7 calculating a ratio of an absolute value of a larger derivative value to an absolute value of a smaller derivative value.

Embodiment 13 is the method of embodiment 10 further comprising:
determining whether the ratio is greater than a pre-selected number; and
in response to determining whether the ratio is greater than a pre-selected number, determining whether the signal is valid.

Embodiment 14 is the method of embodiments 7-13 wherein determining the signal is valid if the signs of the minimum and maximum are different.

Embodiment 15 is the method of embodiments 7-14 wherein determining the signal is invalid in response to determining signs of the minimum and maximum are the same.

Embodiment 16 is the method of embodiments 7-15 wherein the system uses an electrode apparatus located around a patient's torso.

Embodiment 17 is the method of embodiments 7-16 wherein the system is used during ablation of human tissue.

Embodiment 18 is the method of embodiments 7-17 wherein the system is applied to a patient diagnosed with atrial fibrillation.

Embodiment 19 is the method of embodiments 7-18 wherein the system is used during cardiac pacing.

Embodiment 20 is the method of embodiments 7-19 wherein the system is used during cardiac rhythm therapy.

Embodiment 21 is the method of embodiments 7-20 wherein the system is used to locate optimal electrode placement for cardiac therapy.

Embodiment 22 is the method of embodiments 7-21 wherein the system is used to locate optimal electrode placement for cardiac therapy.

Embodiment 23 is a system for use in monitoring cardiac signals comprising:
an electrode apparatus comprising a plurality of electrodes configured to be located proximate tissue of a patient;
display apparatus comprising a graphical user interface, wherein the graphical user interface is configured to present information to a user;
computing apparatus coupled to the electrode apparatus and display apparatus, wherein the computing apparatus is configured to determine whether a signal acquired from a channel associated with an electrode from the plurality of electrodes is valid and sufficiently strong by:
i) calculating a first derivative of the signal;
ii) determining a minimum and maximum of the first derivative;
iii) determining whether signs of the minimum and maximum of the first derivative are different, and if the signs are different, declaring the signal to be invalid; otherwise, if the signs are the same, calculating a ratio of an absolute value of a larger first derivative value to an absolute value of a smaller first derivative value;
iv) determining whether the ratio is greater than a pre-selected number; and in response to determining whether the ratio is greater than the pre-selected number, determining whether the signal is valid.

Embodiment 24 is a system for determining whether a signal is valid or an artifact in a mapping system comprising a processor connected to an electrode and a display apparatus, the electrode located proximate tissue of a patient, wherein the processor is configured to determine whether a signal acquired from a channel associated with the electrode is valid, the system comprising:
means for acquiring a signal from the electrode allows the processor, executing a set of instructions, to perform a set of actions comprising:
i) calculating a first derivative of the signal;
ii) determining a minimum and maximum from the first derivative;
iii) determining whether signs of the minimum and maximum are different; and
in response to determining whether signs of the minimum and maximum are different, displaying on the display apparatus whether the signal is valid.

Embodiment 25 is a machine readable medium containing executable computer program instructions which when executed by a data processing system cause said system to perform a method of displaying cardiac signals, the method comprising:
acquiring a signal from an electrode associated with an electrode apparatus allows the processor, executing a set of instructions, to perform a set of actions comprising:
i) calculating a first derivative of the signal;
ii) determining a minimum and maximum from the first derivative;
iii) determining whether signs of the minimum and maximum are different; and
in response to determining whether signs of the minimum and maximum are different, displaying on the display apparatus whether the signal is valid.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

The invention claimed is:

1. A system for use in monitoring cardiac signals comprising:
an electrode apparatus comprising a plurality of electrodes configured to be located proximate tissue of a patient;
display apparatus comprising a graphical user interface, wherein the graphical user interface is configured to present information to a user;
computing apparatus coupled to the electrode apparatus and display apparatus, wherein the computing apparatus is configured to determine whether a signal acquired from a channel associated with an electrode from the plurality of electrodes is valid and sufficiently strong by:
i) calculating a first derivative of the signal;
ii) determining a minimum and maximum of the first derivative;
iii) determining whether signs of the minimum and maximum of the first derivative are different; and
in response to determining whether the signs of the minimum and maximum of the first derivative are different, displaying on the graphical user interface whether the signal is valid.

2. The system of claim 1, wherein the signal is declared valid when the signs of the minimum and maximum of the first derivative are the same.

3. The system of claim 1 further comprising:
calculating a ratio of an absolute value of a larger first derivative value to an absolute value of a smaller first derivative value.

4. The system of claim 3 further comprising:
determining whether the ratio is greater than a pre-selected number;
and in response to determining whether the ratio is greater than a pre-selected number, determining whether the signal is valid.

5. The system of any of claim 4 wherein in response to determining the signs of the minimum and maximum of the first derivative are different, declaring the signal is valid.

6. The system of any of claim 5 wherein in response to determining the signs of the minimum and maximum of the first derivative are the same, declaring the signal is invalid.

7. The method of claim 1, further comprising:
eliminating any channel or electrode for use in a multi-channel system in which an invalid signal is acquired.

8. A method for determining whether a signal is valid or an artifact in a multichannel mapping system, the multi-channel mapping system comprising a processor connected to an electrode apparatus and a display apparatus, the electrode apparatus located proximate tissue of a patient, wherein the processor is configured to determine whether a signal acquired from a channel associated with an electrode from the plurality of electrodes is valid, the method comprising:
acquiring a signal from an electrode associated with an electrode apparatus allows the processor, executing a set of instructions, to perform a set of actions comprising:
i) calculating a first derivative of the signal;
ii) determining a minimum and maximum from the first derivative;
iii) determining whether signs of the minimum and maximum are different; and
in response to determining whether signs of the minimum and maximum are different, displaying on the display apparatus whether the signal is valid.

9. The method of claim 8, wherein the signal is declared valid in response to determining the signs of the minimum and maximum are the same.

10. The method of claim 8, wherein the signal is declared invalid in response to determining the signs of the minimum and maximum are different.

11. The method of claim 10, wherein the invalid signal is determined to be an artifact.

12. The method of claim 11 further comprising:
determining whether the ratio is greater than a pre-selected number; and
in response to determining whether the ratio is greater than a pre-selected number, determining whether the signal is valid.

13. The method of claim 8 further comprising:
calculating a ratio of an absolute value of a larger derivative value to an absolute value of a smaller derivative value.

14. The method of claim 8 wherein determining the signal is valid if the signs of the minimum and maximum are different.

15. The method of claim 8 wherein determining the signal is invalid in response to determining signs of the minimum and maximum are the same.

16. The method of claim 8 wherein the system uses an electrode apparatus located around a patient's torso.

17. The method of claim 8 wherein the system is used during ablation of human tissue.

18. The method of claim 8 wherein the system is applied to a patient diagnosed with atrial fibrillation.

19. The method of claim 8 wherein the system is used during cardiac pacing.

20. The method of claim 8 wherein the system is used during cardiac rhythm therapy.

21. The method of claim 8 wherein the system is used to locate optimal electrode placement for cardiac therapy.

22. The method of claim 8 wherein the system is used to locate optimal electrode placement for cardiac therapy.

23. A system for use in monitoring cardiac signals comprising:
- an electrode apparatus comprising a plurality of electrodes configured to be located proximate tissue of a patient;
- display apparatus comprising a graphical user interface, wherein the graphical user interface is configured to present information to a user;
- computing apparatus coupled to the electrode apparatus and display apparatus, wherein the computing apparatus is configured to determine whether a signal acquired from a channel associated with an electrode from the plurality of electrodes is valid and sufficiently strong by:
  - i) calculating a first derivative of the signal;
  - ii) determining a minimum and maximum of the first derivative;
  - iii) determining whether signs of the minimum and maximum of the first derivative are different, and if the signs are different, declaring the signal to be invalid; otherwise, if the signs are the same, calculating a ratio of an absolute value of a larger first derivative value to an absolute value of a smaller first derivative value;
  - iv) determining whether the ratio is greater than a pre-selected number; and in response to determining whether the ratio is greater than the pre-selected number, determining whether the signal is valid.

24. A system for determining whether a signal is valid or an artifact in a mapping system comprising a processor connected to an electrode and a display apparatus, the electrode located proximate tissue of a patient, wherein the processor is configured to determine whether a signal acquired from a channel associated with the electrode is valid, the system comprising:
- means for acquiring a signal from the electrode allows the processor, executing a set of instructions, to perform a set of actions comprising:
  - i) calculating a first derivative of the signal;
  - ii) determining a minimum and maximum from the first derivative;
  - iii) determining whether signs of the minimum and maximum are different; and
- in response to determining whether signs of the minimum and maximum are different, displaying on the display apparatus whether the signal is valid.

25. A non-transitory machine readable medium containing executable computer program instructions which when executed by a data processing system cause said system to perform a method of displaying cardiac signals, the method comprising:
- acquiring a signal from an electrode associated with an electrode apparatus allows the processor, executing a set of instructions, to perform a set of actions comprising:
  - i) calculating a first derivative of the signal;
  - ii) determining a minimum and maximum from the first derivative;
  - iii) determining whether signs of the minimum and maximum are different; and
- in response to determining whether signs of the minimum and maximum are different, displaying on the display apparatus whether the signal is valid.

\* \* \* \* \*